US011696976B2

(12) United States Patent
Kumta et al.

(10) Patent No.: US 11,696,976 B2
(45) Date of Patent: *Jul. 11, 2023

(54) DEGRADABLE MAGNESIUM-BASED IMPLANT DEVICES FOR BONE FIXATION

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Abhijit Roy, Pittsburgh, PA (US); Da-Tren Chou, Bay Village, OH (US); Daeho Hong, Ramsey, NJ (US); Vijay S. Gorantla, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/750,219

(22) PCT Filed: Aug. 22, 2016

(86) PCT No.: PCT/US2016/048035
§ 371 (c)(1),
(2) Date: Feb. 5, 2018

(87) PCT Pub. No.: WO2017/035072
PCT Pub. Date: Mar. 2, 2017

(65) Prior Publication Data
US 2018/0221545 A1  Aug. 9, 2018

Related U.S. Application Data

(60) Provisional application No. 62/208,044, filed on Aug. 21, 2015.

(51) Int. Cl.
*A61L 31/14* (2006.01)
*A61L 31/02* (2006.01)
*C22C 23/04* (2006.01)

(52) U.S. Cl.
CPC .......... *A61L 31/148* (2013.01); *A61L 31/022* (2013.01); *C22C 23/04* (2013.01); *A61L 2430/02* (2013.01)

(58) Field of Classification Search
CPC ............................. A61L 31/148; C22C 23/04
See application file for complete search history.

(56) References Cited

U.S. PATENT DOCUMENTS 9,863,020 B2 * 1/2018 Kumta .................... C22C 23/06
2008/0031765 A1 2/2008 Gerold et al.
(Continued)

FOREIGN PATENT DOCUMENTS

CN 104906638 A * 9/2015
JP 2007319895 A * 12/2007
(Continued)

OTHER PUBLICATIONS

English Translation of JP-2007319895-A (Year: 2007).*
(Continued)

*Primary Examiner* — Anthony J Zimmer
*Assistant Examiner* — Sean P. O'Keefe
(74) *Attorney, Agent, or Firm* — Carol A. Marmo; Eckert Seamans Cherin & Mellott, LLC

(57) ABSTRACT

The invention relates to biodegradable, magnesium alloys, compositions and composites, methods for their preparation and applications for their use as implantable medical devices in load-bearing conditions. The magnesium alloys are composed of alloying elements selected from yttrium, calcium, zirconium, zinc, and strontium, with the remainder being magnesium and impurities due to production, and are pre-
(Continued)

pared by melting together the elements and casting the resulting melted mixture. In certain embodiments, the methods of preparation include solution treatment and hot extrusion.

2 Claims, 13 Drawing Sheets

(56) References Cited

U.S. PATENT DOCUMENTS

| | | | |
|---|---|---|---|
| 2008/0033530 A1 | 2/2008 | Zberg et al. | |
| 2008/0311423 A1* | 12/2008 | Numano | B22D 11/001 |
| | | | 428/687 |
| 2009/0162242 A1* | 6/2009 | Inoue | B22D 21/007 |
| | | | 164/122 |
| 2011/0192500 A1 | 8/2011 | Uggowitzer et al. | |
| 2013/0144290 A1* | 6/2013 | Schiffl | C22F 1/06 |
| | | | 606/62 |
| 2014/0248288 A1 | 9/2014 | Kumta et al. | |
| 2016/0022863 A1* | 1/2016 | Decker | A61L 31/022 |
| | | | 148/420 |

FOREIGN PATENT DOCUMENTS

| | | | | |
|---|---|---|---|---|
| KR | 10-2008-0027202 A | 3/2008 | | |
| WO | WO-2013052791 A2 * | 4/2013 | | C22C 23/06 |

OTHER PUBLICATIONS

Kim, Jeong Min, Bong Koo Park, Joong Hwan Jun, Ki Tae Kim, and Woon Jae Jung. "Formability of Mg—Zn—Zr Based Alloy Sheets at Elevated Temperatures." Key Engineering Materials 345-346 (Aug. 2007): 21-24 (Year: 2007).*

Fan, Jun, et al. "Microstructure, mechanical properties, in vitro degradation and cytotoxicity evaluations of Mg—1.5 Y—1.2 Zn—0. 44 Zr alloys for biodegradable metallic implants." Materials science and engineering: C 33.4 (2013): 2345-2352. (Year: 2013).*

* cited by examiner

DEGRADABLE MAGNESIUM-BASED IMPLANT DEVICES FOR BONE FIXATION

CROSS-REFERENCE TO RELATED APPLICATIONS

This application claims priority under 35 U.S.C. § 119(e) from U.S. provisional patent application No. 62/208,044, entitled "Degradable Magnesium-Based Implant Devices for Bone Fixation" and filed on Aug. 21, 2015, the contents of which are incorporated herein by reference.

GOVERNMENT SUPPORT AND FUNDING

This invention was made with government support under grant #0812348 awarded by the National Science Foundation (NSF). The government has certain rights in the invention.

FIELD OF THE INVENTION

The invention relates to magnesium alloy materials, methods for their preparation, and uses as implant devices for bone fixation in load-bearing conditions. The invention is particularly suitable for use in fabricating biodegradable compositions and composites, and medical devices for implantation into a body of a patient, such as for example, orthopedic, craniofacial and cardiovascular implant devices.

BACKGROUND OF THE INVENTION

Bone fractures generally are common injuries among patients of all ages and may account for more than ten million annual hospital visits in the United States. These fractures, small or long bone, are projected to increase due to the burgeoning geriatric population with concomitant increases in the prevalence of obesity and osteoporosis. In the pediatric population, bone fractures are also extremely common, and may account for about fifteen percent of all injuries.

Management of bone fractures may require open or closed reduction with or without internal fixation devices, such as, Kirschner wires (K-wires), pins, intramedullary rods or nails, cerclage wire, plates and screws to stabilize bone fragments, and facilitate healing. K-wires are used by either an open or a percutaneous implantation route to stabilize fracture fragments by driving a wire between two pieces of bone to be fixed. The use of K-wires is an established practice for reconstructive surgery, such as, fixation of vascularized free fibular grafts or premaxillary segments in bilateral cleft lip surgery, to stabilize zygomatic arch fractures or nasal septal fixation in the case of a saddle nose, as well as mandibular reconstruction.

In bone reconstruction procedures, it is often necessary to hold the bone or fragments of bone together to create a stable environment for healing to occur. This is typically done with metal wires or cables using a technique referred to as "cerclage". A cerclage wire or cable is coiled around a bone or bony fragments to hold them together to allow them to heal. Cerclage has numerous applications in orthopedics as a primary method of fracture fixation and as a supplement to other forms of fixation. Traditionally, these K-wires, pins, nails and cerclage wires are derived from inert and non-degradable cobalt-chromium, stainless steel and titanium alloys. These metals have been traditionally selected for fracture fixation because of their advantageous biomechanical and biocompatibility parameters. The high mechanical strength of these metals makes them beneficial for load-bearing applications. However, there have also been disadvantages associated with these metals. For example, a mismatch in mechanical properties compared to cortical bone often causes stress shielding effects that tend to damage surrounding tissues. Further, these metals have been associated with complications including, but not limited to, pin-tract infections, non-union, mal-union, local soft tissue reaction, nerve injury, broken metal wires or cables, wire migration and morbidity related to secondary procedures or the need for device removal. Degradable polymers such as PLGA/PLL have been used in surgical hardware. However, these devices have been found to be mechanically inferior and not suitable for load-bearing (stress, shear, torsional or compressive forces) applications, such as, mandibular and long bone fixation.

Magnesium alloys have recently emerged as a new class of biodegradable materials for orthopedic applications. Unlike inert titanium or stainless steel devices, biodegradable Mg hardware is designed to repair bone fractures and resorb over time after bone healing. Compared to conventionally used non-degradable metals, magnesium alloys have biomechanical properties more similar to natural bone. Magnesium is an essential trace element in the human body, exists in bone naturally and has higher mechanical strength compared to biodegradable polymers. Degradable magnesium is biocompatible, non-toxic and osteoconductive. Recent reports also suggest osteoinductive characteristics of magnesium. Magnesium alloys are also completely resorbable in the body, which can eliminate the need for secondary removal surgeries, and promote enhanced bone reorganization as a result of the gradual increase in load-to-bear associated with device degradation.

Furthermore, the properties of magnesium alloys can be tailored to exhibit desired mechanical and degradation properties for optimal healing. Corrosion is the degradation mechanism common to biodegradable magnesium alloys. During the reaction of magnesium with water, magnesium hydroxide and hydrogen gas are produced. Rapid corrosion of magnesium alloys can develop gas pockets near an implantation site and, may lead to patient discomfort and pain due to the consequent pH change, and the imminent hydrogen gas evolution state. Also, rapid corrosion can cause immature mechanical failure of the device during the initial fracture healing process. Thus, to overcome rapid corrosion of magnesium, alloy compositions and their microstructure may be tailored by the selection of particular alloy systems and processing conditions.

Although there are non-load bearing fixation devices composed of biodegradable magnesium alloys, there is a need in the art to design and develop improved biodegradable hardware for implementation in extremity and craniofacial, orthopedic and cardiovascular fixation, such as, resorbable metal-based K-wires, pins and cerclage wires. Therefore, in accordance with the invention, there is provided bioresorbable K-wires, pins, nails and cerclage wired based on novel magnesium alloy compositions, for use under load-bearing conditions, which can circumvent one or more of the above problems associated with indwelling hardware or other fixation.

SUMMARY OF THE INVENTION

In one aspect, the invention provides a biodegradable, magnesium alloy, consisting of from about 0.5 weight percent to about 4.0 weight percent of yttrium; from greater than zero to about 1.0 weight percent of calcium; from about from about 1.0 weight percent to about 6.0 weight percent of zinc; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

In another aspect, the invention provides a biodegradable, magnesium alloy consisting of from about 1.0 weight percent to about 6.0 weight percent of zinc; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

In still another aspect, the invention provides a biodegradable, magnesium alloy consisting of from about 0.5 weight percent to about 4.0 weight percent of yttrium; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

BRIEF DESCRIPTION OF THE DRAWINGS

A further understanding of the invention can be gained from the following description of the preferred embodiments when read in conjunction with the accompanying figures.

DETAILED DESCRIPTION OF THE PREFERRED EMBODIMENTS

Figure 1:
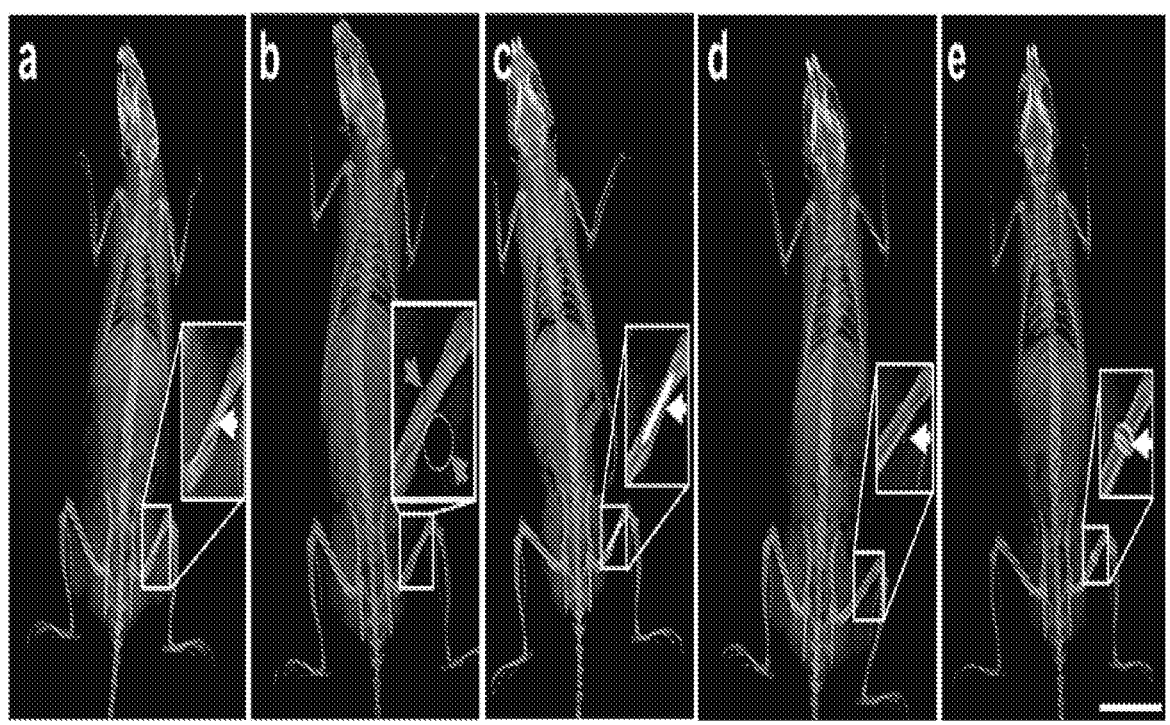
FIG. 1 is a plurality of images showing one-week post-operative x-ray images of implanted sharpened pins: (a) WZ42 magnesium alloy, (b) fracture misalignment and dead spaces near the WZ42 implants, (c) Ti6Al4V in the right femur, (d) WZ42 magnesium alloy and (e) Ti6Al4V in the right femur, in accordance with certain embodiments of the invention.

The invention relates to novel, biodegradable magnesium alloys, compositions and composites. Further, the invention relates to articles, such as medical devices for implantation into a body of a patient, which are constructed or fabricated from the biodegradable magnesium alloys, compositions, and composites of the invention, for load-bearing conditions. A wide variety of medical implant devices are known in the art and include, but are not limited to, Kirschner wires (K-wires), pins, intramedullary rods or nails, cerclage wires and the like. Moreover, the invention relates to methods of preparing these biodegradable, magnesium alloys, compositions and composites for use in medical applications, such as but not limited to, orthopedic, craniofacial and cardiovascular surgery.

In addition to biodegradability, the magnesium alloys of the invention include at least one of the following characteristics: biocompatibility, corrosion resistance, cell attachment, viability and mechanical strength. The magnesium alloys can include alloying elements that are pre-selected and present in particular amounts, such that one or more desired characteristics, such as, but not limited to degradation and mechanical strength, may be achieved.

In addition, to component selection in specific percentages, desired characteristics, such as but not limited to, degradation and strength of the magnesium alloys can be controlled or tailored by post-processing and microstructural modifications. For example, following melting and casting of the magnesium alloys, post-processing steps of solution treatment and hot extrusion can be implemented to impart grain refinement to further improve and augment the mechanical properties, and corrosion resistance of the magnesium alloys.

The magnesium alloys can contain unique combinations of elements, which include precipitates arranged in a long period stacking order (LPSO), resulting in high strength.

In certain embodiments, the invention includes controlling corrosion rate and improving mechanical properties of magnesium alloys through the introduction of additional, e.g., alloying, elements and processing conditions. It has been found that magnesium corrosion and mechanical properties are affected by specific alloying elements.

In certain embodiments of the invention, the biodegradable, magnesium alloys include alloying elements selected from yttrium, calcium, zinc, zirconium and strontium. As stated above herein, the specific alloying elements selected and the amounts of each can vary. In general, the amounts of each of the alloying elements are selected such that the resulting compositions are within acceptable non-toxic limits, sufficiently biocompatible for implantation into a body of a patient, and degradable over a period of time so that the implantation device does not remain in the body of the patient for prolonged periods of time, e.g., not beyond the period of time when there is a medical need for the implantation device. An implantation device fabricated in accordance with the invention will degrade and preferably completely dissolve within an acceptable time frame. Acceptable non-toxic limits and degradation can vary and can depend on particular physical and physiological characteristics of the patient, the particular in vivo site of the implantation device, and the particular medical use of the implantation device.

In certain embodiments, the magnesium alloys include yttrium, zinc, calcium and zirconium; or yttrium, zinc, calcium, zirconium and strontium; or yttrium, zinc and zirconium; or yttrium, zinc, zirconium and strontium; or yttrium, zirconium and strontium, with a remainder of magnesium and impurities due to production. In these embodiments, yttrium constitutes from about 0.5 weight percent to about 4.0 weight percent; calcium constitutes from greater than zero to about 1.0 weight percent; zirconium constitutes from greater than zero to about 1.0 weight percent; zinc constitutes from about 1.0 weight percent to about 6.0 weight percent; strontium constitutes from greater than zero to about 6.0 weight percent or from about 0.10 weight percent to about 6.0 weight percent, with the remainder being magnesium and impurities due to production, based on the total weight of the alloy.

In one embodiment, the biodegradable, magnesium alloy consists of from about 0.5 weight percent to about 4.0 weight percent of yttrium; from greater than zero to about 1.0 weight percent of calcium; from about 1.0 weight percent to about 6.0 weight percent of zinc; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

In another embodiment, the biodegradable, magnesium alloy consists of from about 1.0 weight percent to about 6.0 weight percent of zinc; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

In still another embodiment, the biodegradable, magnesium alloy consists of from about 0.5 weight percent to about 4.0 weight percent of yttrium; from greater than zero to about 1.0 weight percent of zirconium; from greater than zero to about 6.0 weight percent of strontium; optionally from about 1.0 weight percent to about 9.0 weight percent aluminum; optionally from about 0.1 weight percent to about 1.0 weight percent of manganese; optionally from about 0.25 weight percent to about 1.0 weight percent of silver; optionally from about 0.1 weight percent to about 1.0 weight percent of cerium; and a balance of magnesium and impurities due to production, based on total weight of the alloy.

Without intending to be bound by any particular theory, it is believed that the presence of yttrium can contribute to the improved mechanical strength and corrosion resistance; calcium can prevent oxidation during the casting of the alloy; zirconium can act as a grain refiner and improve mechanical properties of the compositions; and strontium can stimulate bone formation. The amounts of magnesium and the alloying elements may be specified and adjusted such as to control at least one of corrosion resistance, biodegradation, biocompatibility, toxicity, cell attachment, mechanical strength and flexibility.

Further, in certain embodiments, one or more other alloying elements may be added to the magnesium alloys to impart additional characteristics and properties. These other alloying elements can be selected from those known in the art, and can include, but are not limited to, cerium, aluminum, manganese, and silver, in amounts that can vary. One or more of cerium, aluminum, manganese and silver may be present in the magnesium alloy, wherein each is present in an amount of from greater than zero to about 1.0 percent by weight based on total weight of the alloy.

In certain embodiments, aluminum constitutes from about 1.0 weight percent to about 9.0 weight percent based on the total weight of the alloy. In other embodiments, aluminum constitutes from about 2.0 weight percent to about 9.0 weight percent based on the total weight of the alloy.

In certain embodiments, manganese constitutes from about 0.1 weight percent to about 1.0 weight percent based on the total weight of the alloy. In other embodiments, manganese constitutes from about 0.2 weight percent to about 1.0 weight percent based on the total weight of the alloy.

In certain embodiments, silver constitutes from about 0.10 weight percent to about 1.0 weight percent based on the total weight of the alloy. In other embodiments, silver constitutes from about 0.25 weight percent to about 1.0 weight percent based on the total weight of the alloy.

In certain embodiments, cerium constitutes from about 0.1 weight percent to about 1.0 weight percent based on the total weight of the alloy. In other embodiments, cerium constitutes from about 0.5 weight percent to about 1.0 weight percent based on the total weight of the alloy.

Non-limiting examples of medical devices in which the magnesium alloys, compositions and composites of the invention can be used include, but are not limited to wires, such as, Kirchner wires (K-wires), pins, intramedullary rods or nails, cerclage wires and related devices, including, plates, meshes, staples, screws, tacks, suture anchors, tubular mesh, coils, x-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, intercranial aneurism device, tracheal stents, nerve guides and surgical implants.

The biodegradable, magnesium alloys of the invention can be prepared using various methods and processes. In general, conventional melting and casting methods, and processes are employed. It is known in the art of metallurgy that casting is a production technique in which a metal or a mixture of metals, e.g., metal alloy, is heated until molten and then poured into a mold, allowed to cool, and thereby solidified. In certain embodiments, a melted or molten mixture of metals or metal alloy is poured into a mild steel/copper mold at a temperature from ambient, e.g., room temperature, to 500° C.

Casting of the magnesium-based alloys of the invention can be carried out using any conventional casting procedures known in the art, such as, but not limited to, sand casting, gravity casting, permanent mold casting, direct chill casting, centrifugal casting, low/high pressure die casting, squeeze casting, continuous casting, vacuum casting, plaster casting, lost foam casting, investment casting, and lost wax casting. It is believed that the particular process used for casting may affect the properties and characteristics of the cast alloy. Further, it is believed that the temperature at which the melting procedure is performed may also affect the alloy. Thus, the temperature may be carefully selected so as to maintain or achieve desired properties of the magnesium alloy.

The resulting cast can be subjected to various forming and finishing processes known in the art. Non-limiting examples of such processes include, but are not limited to, solution treating, quenching, extruding, e.g., hot extruding, homogenizing, forging, rolling, equal channel angular extrusion, stamping, deep-drawing, wire-drawing, polishing (by mechanical and/or chemical means), surface treating (to form a superficial layer on the surface), machining, e.g., lathe machining, and combinations thereof.

In certain embodiments, the invention includes melting (e.g., heating at an elevated temperature) and casting the magnesium and alloying elements, followed by solution treatment and hot extrusion. The hot extrusion can be carried out at a temperature of about 450° C. with an extrusion ratio of 30:1. The extruded alloy can be machined, such as, by lathe machining, to form an implant device, e.g., pins or wires. The implant device is typically washed, dried and sterilized prior to implantation into the patient.

Further, prior to solidification, the molten mixture or alloy may be tested to determine the amount of the various components therein and therefore, to provide an opportunity to adjust the amounts as desired prior to solidification.

One or both or the melting and casting steps may be performed under a protective atmosphere to preclude, minimize or reduce oxidation/decomposition of the elements in the material. In particular, it is desirable to preclude, minimize or reduce the oxidation/decomposition of magnesium. The protective atmosphere can include, but is not limited to, argon, sulfur hexafluoride, carbon dioxide, dry air and mixtures thereof.

In certain embodiments, subsequent to the casting process, the magnesium-containing cast may be subjected to homogenization. Without intending to be bound by any particular theory, it is believed that homogenization treatment can cause the spreading of, or more even or uniform distribution of, impurities, secondary phase(s), and intermetallic phases, if present therein. The resulting alloy may be in the form of a single phase, solid solution.

Detailed exemplary procedures for melting, casting, solution treating and extruding are depicted in the following examples.

Additional objects, advantages and novel features of the invention may become apparent to one of ordinary skill in the art based on the following examples, which are provided for illustrative purposes and are not intended to be limiting.

EXAMPLES

Example 1

This experiment evaluated the safety and efficacy of a novel Mg—Y—Zn—Zr—Ca alloy compared to non-degradable Ti6Al4V, over a 14-week follow-up, implanted as pins to fix a full osteotomy in rat femurs and as wires wrapped around the outside of the femurs as a cerclage. To assess systemic toxicity, blood cell count and serum biochemical tests were performed. Livers and kidneys were harvested to observe histomorphological alterations and accumulation of alloying elements. Hard and soft tissue adjacent to the fracture site were examined using Goldner's Trichrome and alkaline phosphatase staining. Degradation behavior of the Mg alloys was determined using μCT scans to assess alloy degradation and bone morphology. Blood testing exhibited no significant changes arising from the Mg alloy compared to the control groups. No recognizable differences in the morphology of liver and kidney tissue, and no accumulation of Mg, Zn, and Ca in these organs were observed. Corrosion occurred gradually, with degradation slowing after 2 weeks, with points of high stress observed near the fracture site ultimately resulting in Mg alloy pin fracture. Nevertheless, normal bone healing was observed in femurs fixed with the Mg alloy that was confirmed by the presence of osteoids, osteoblast activity, and new bone formation. These results demonstrate the feasibility of the Mg—Y—Zn—Zr—Ca alloy for orthopedic and craniofacial fracture fixation applications.

A fully load-bearing model was employed, wherein a full fracture of the rat femur was fixed using only the implant pins of the Mg alloy, Mg—Y—Zn—Zr—Ca (WZ42), and the performance was compared to pins machined from the common medical titanium alloy, Ti6Al4V. The model bears the characteristics of exposing the system to considerable stress in the absence of any external immobilization, since the animal is allowed to ambulate immediately following surgery combined with dual exposure to the vasculature creating ideal conditions for stress corrosion. Moreover, this model selected has conceptual similarities mimicking orthopedic fixation devices such as Kirschner wires (K-wires) and Steinmann pins—thin rods that are drilled or tapped through bone fracture fragments to maintain the anatomical congruity and biomechanical stability required for optimal bone healing. Currently used stainless steel and titanium K-wires are removed after the bone has healed, necessitating a secondary removal procedure the patient must endure. To allow for easy removal of the K-wire during this secondary procedure, the ends of the rods are usually left outside the skin, forming a "pin-tract" that may act as a conduit for causing infection. Other complications arising from these fixation devices include nerve injury, pain, osteomyelitis, and migration. These shortcomings of K-wires and other common orthopedic devices derived customarily from existing inert metals could thereby be avoided through the use of degradable Mg alloys.

In addition to this challenging load-bearing model with intramedullary fracture fixation pins, WZ42 wires were wrapped around the mid-diaphyseal region of unfractured femurs forming a cerclage cuff to compare degradation and tissue response to the Mg alloy implanted in different regions—intramedullary versus over the cortical bone. With these two implants, in vivo corrosion, bone healing, and host response was assessed to provide an overall evaluation of the degradable WZ42 magnesium alloy when utilized in orthopedic device applications.

Materials and Methods

Preparation of Mg—Y—Zn—Zr—Ca Implants

The procedure for melting and casting the WZ42 alloy (nominal composition of Mg-4.0% Y-2.0% Zn-1.0% Zr-0.6% Ca in wt. %) was conducted. Alloying elements in pure form and contained in Mg master alloys were melted in an electrical resistance furnace (Wenesco Inc., Chicago, Ill.) under the protection of Ar+1.5% SF6 cover gas and cast into a cylindrical mild steel mold preheated to 500° C. after stirring and holding for 30 minutes to achieve dispersion of Zr. After casting, a solution treatment of 400° C. was applied for 20 hours and the ingot was quenched to room temperature in water to increase the alloy's ductility, and homogenize the secondary phases. The ingot was extruded at a temperature of 450° C. with an extrusion ratio of 30. The extruded WZ42 and control material Ti6Al4V (Goodfellow Corporation, Coraopolis, Pa.) were lathe machined into pins with dimensions of 15 mm length×1.66 mm diameter and, wires of 20 mm length and 0.68 mm diameter. The implants were sonicated in washes of acetone and isopropanol and dried before undergoing sterilization by gamma radiation ($2\times10^6$ cGy, 23.5 Gy/min, cesium 137 source, Mark I 68, J L Shepherd and Associates, San Fernando, Calif.).

Surgical Model and Study Protocol

All the animal experiments were approved by the University of Pittsburgh's Institutional Animal Care and Use Committee (IACUC). Before surgery, female Sprague-Dawley rats weighing 250-300 g were anesthetized by inhalation of isoflurane at a concentration of 2-5% for initiation of sedation, and 0.25-4% for maintenance. Only the right hind limb of each rat was operated. First, the right hind limbs were shaved and disinfected, and an approximately 2 cm incision was made over the dorsolateral right femur. The skin and mid-diaphyseal region of the right femurs were exposed through a lateral approach. A complete femoral osteotomy was created using a circular saw. The WZ42 or Ti6Al4V fixation pins were inserted first into the intramedullary space of the distal portion of the fractured femur, then inserted into the intramedullary space of the proximal femur, with the fracture approximated. In the case of the wire cuffs, the right femur was not cut, and the wires were wrapped around the midsection of the diaphysis over the periosteum and pressed against the bone to avoid any translation along the shaft of the femur or migration. After the samples were implanted, the fascia and muscles were closed with 3.0 VICRYL (J315), and the skin closed using non-absorbable monofilament 3.0 polyamide sutures.

Post-operative pain and distress was observed daily for expressions of stress and behavioral abnormalities, changes in movement, food, and water intake. Furthermore, the right hind limbs were clinically observed on a daily basis for signs of infection, wound dehiscence, presence of gas pockets or abnormal posture/thigh anatomy.

Groups of five animals for both WZ42 and Ti6Al4V pins were used for each time point of 2, 8, and 14 weeks postoperative for blood values, tissue samples (liver, kidney, femurs with surrounding soft tissues), and micro-CT analysis, and groups of 6 animals were implanted with wire cuffs with a single time point of 14 weeks for toxicological assessment, as displayed in Table 1.

TABLE 1

Summary of number of rats in each group at time points used in study.

| | Time point: | | | |
|---|---|---|---|---|
| | Pre-operative | 2 weeks | 8 weeks | 14 weeks | 14 weeks |
| | | Intramedullary Pin | | | Cuff |
| Ti6Al4V | | 5 | 5 | 5 | 6 |
| WZ42 | | 5 | 5 | 5 | 6 |
| Naïve | 3 | | | | |

Immediately following sacrifice, the liver, kidney, and experimental group femurs were collected and stored for further analysis as described in the following sections. Three rats receiving no surgery were also sacrificed to serve as the naïve control group.

X-Ray Imaging

Conventional X-ray imaging was performed on rats one week post-operatively to examine the position of the implants and stability of the fracture. For that purpose, the animals were anesthetized with isoflurane.

Blood-Cell Count and Serum Biochemical Measurements

Blood samples were collected from animals before operation (baseline) under anesthesia by tail snip and terminally (2, 8, and 14 weeks post-implantation) by cardiac puncture. Whole blood cell counts were performed by Marshfield Labs (Cleveland, Ohio) using a Sysmex XT2000i Automated Hematology Analyzer (Sysmex Corporation, Kobe, Japan) with provided reference ranges. Serum samples were obtained by centrifuging collected blood at 2,000 rpm for 10 minutes at 4° C. Serum biochemical tests were conducted by Marshfield Labs using an Olympus AU chemistry analyzer (Olympus Corporation, Tokyo, Japan) with reported reference ranges established by Marshfield Labs.

Micro-Computed Tomography Imaging

Plastic embedded rat femurs were used for high resolution micro-computed tomography (μCT) scanning. WZ42 alloy samples were scanned with continuous rotation μCT at 10.5 μm voxel size before implantation and, after retrieval along with surrounding tissue post-operatively at 2, 8, and 14 weeks. The reconstructed data sets were used to generate a 3D volume from which the remaining metal rod was distinguished from the surrounding degradation products and bone by using a histogram of grey values based on densities. A density threshold for the metal pins was used to isolate the volume of remaining magnesium alloy from the surrounding material and compared to the volume of the pins before implantation to estimate in vivo corrosion rate using the following equation adapted from the standard ASTM G31:

$$C=(K \times V)/(A \times T)$$

wherein C is the corrosion rate (mm year$^{-1}$ or mmpy), the constant K is $8.76 \times 10^4$, V is the volume loss (cm$^3$), A is the initial sample area exposed (cm$^2$), and T is the time of exposure (h).

Histological Preparation and Analysis

Specimens of liver and kidney were fixed in 10% neutral buffered foinialin, dehydrated, then infiltrated and embedded in paraffin. They were stained with hematoxylin and eosin (H&E) and evalated for cell infiltration, tissue morphology and pathological changes due to degradation and clearance of the WZ42 alloy in these critical visceral organs.

Femurs were fixed in 70% ethanol, dehydrated, infiltrated and embedded in Osteo-Bed Plus methyl methacrylate-based embedding kit (Polysciences, Inc., Warrington, Pa.). The plastic blocks were sectioned with a rotary microtome (Leica RM 2255, Leica Biosystems, Buffalo Grove, Ill.) and stained using Goldner's Trichrome and alkaline phosphatase stains to observe bone morphology and, osteoblast activity at the site of fracture and surrounding the implants.

Tissue Digestion and Elemental Analysis

Liver and kidney tissues were digested to allow for measurement of elemental concentration using inductively coupled plasma with optical emission spectroscopy (ICP-OES). First, tissues were dried at 70° C. for 24 hours, then homogenized and weighed. The samples were then digested by immersion in 20 ml nitric acid/g tissue for 6 hours at 70° C., followed by the addition of 4 ml hydrogen peroxide/g tissue for 1 hour and 4 ml sulfuric acid/g tissue for 1 hour. Samples were then diluted 50× in ultra-pure deionized water (purified using Milli-Q Academic, Millipore, Billerica, Mass.), filtered in 0.45 μM syringe filters, and analyzed for Mg and alloying element concentration by ICP-OES (ICP-OES, iCAP duo 6500 Thermo Fisher, Waltham, Mass.).

Statistical Analysis

Statistical analysis was conducted using SPSS Statistics 17.0 (SPSS Inc., Chicago, Ill.). Differences between the groups were analyzed using one-way ANOVA with post-hoc testing using Gabriel's pairwise test. $P<0.05$ was accepted as a statistically significant difference between means.

Results

Fixation of Femoral Fracture Using Mg—Y—Zn—Zr—Ca Alloy Pin

The intramedullary pins were successfully inserted into the fractured femurs during surgery with the fractures being approximated as seen in the 1-week postoperative X-ray images of FIG. 1a-c, despite the slight mismatches between the pin diameter and the diameter of the intramedullary cavity observed in 68% (13 of 19) of cases (FIG. 1b, arrow) owing to manual surgical placement resulting in a small gap or misalignment in the two sides of the fractured femur. All the wire cuffs maintained their position wrapped around the femur as shown in FIGS. 1d and e.

Small pockets of dead space (FIG. 1b, arrow) were observed in the 1-week X-rays of 73% (19 of 26) of the rats with implanted WZ42 alloy pins or cuffs, likely caused by hydrogen gas evolved from the degrading Mg implants. Despite their presence in the X-ray images, no bulges in the skin in the hind limb of the rats were observed during the frequent visual inspections of the rats. The rats had regained mobility by postoperative day 7.

Systemic Toxicity to Mg—Y—Zn—Zr—Ca Implants

Total blood cell counts are listed in Table 2, which generally did not reveal any disturbance in the blood count values, with parameters remaining within references ranges or near pre-operation levels.

TABLE 2

Average blood cell counts of naïve animals and animals implanted with WZ42 and Ti6Al4V alloy pins and cuffs at 2, 8, and 14 weeks after implantation.

| | Implantation time | Red Blood Cell Count | Hemoglobin | Platelet Count | White Blood Cell Count |
|---|---|---|---|---|---|
| | | $10^6$/uL | g/dL | $10^3$/uL | $10^3$/uL |
| Ref. ranges | | (7.00-9.00) | (13.7-16.8) | (680-1280) | (1.1-7.5) |
| Naive | | 7.4 ± 0.3 | 14.1 ± 0.9 | 618.3 ± 200.6 | 6.8 ± 2.3 |
| WZ42 pin | 2 weeks | 8.0 | 14.3 | 839.0 | 8.6 |
| Ti6Al4V pin | 2 weeks | 7.8 | 14.9 | 656.0 | 9.0 |
| WZ42 pin | 8 weeks | 7.4 ± 0.5 | 13.8 ± 1.2 | N/A | 6.8 |
| Ti6Al4V pin | 8 weeks | 7.4 ± 0.3 | 14.2 ± 0.4 | 637.8 ± 168.6 | 5.9 ± 1.6 |
| WZ42 pin | 14 weeks | 7.7 ± 0.4 | 14.2 ± 0.5 | 595.8 ± 179.8 | 5.9 ± 2.1 |
| Ti6Al4V pin | 14 weeks | 7.5 ± 0.4 | 14.0 ± 0.7 | 563.0 ± 164.5 | 5.9 ± 2.7 |
| WZ42 cuff | 14 weeks | 7.1 ± 0.2 | 13.9 ± 0.4 | 461.0 ± 56.6 | 2.2 ± 1.0 |
| Ti6Al4V cuff | 14 weeks | 7.6 ± 0.4 | 13.8 ± 0.7 | 637.0 ± 96.5 | 5.8 ± 1.4 |

Small differences from the reference ranges or naïve levels were observed for low platelet counts in the WZ42 cuff group, and WZ42 and Ti6Al4V pins at 14 weeks. Elevated postoperative white blood cell counts were seen at 2 weeks for both WZ42 and Ti6Al4V pins.

TABLE 3

Average values of serum metabolic parameters of naive animals and animals implanted with WZ42 and Ti6Al4V alloy pins and cuffs at 2, 8, and 14 weeks after implantation.

| | | Name | | | |
|---|---|---|---|---|---|
| | | Glucose | ALT(GPT) | ALP | Total Bilirubin |
| | | | Units | | |
| | Implantation | mg/dL | U/L | U/L | mg/dL |
| | | | Ref. ranges | | |
| | time | (70-308) | (59-166) | (232-632) | (0.0-0.1) |
| Unoperated | | 181.2 ± 19.8 | 55.8 ± 9.2 | 175.2 ± 20.3 | 0.17 ± 0.10 |
| WZ42 pin | 2 weeks | 155.8 ± 26.7 | 57.3 ± 7.9 | 148.3 ± 13.6 | 0.18 ± 0.05 |
| Ti6Al4V pin | 2 weeks | 322.0 ± 94.4 | 66.3 ± 20.3 | 151.2 ± 21.8 | 0.14 ± 0.05 |
| WZ42 pin | 8 weeks | 294.5 ± 205.0 | 80.4 ± 13.9 | 163.2 ± 30.4 | 0.24 ± 0.05 |
| Ti6Al4V pin | 8 weeks | 204.8 ± 75.9 | 54.5 ± 17.9 | 201.5 ± 40.2 | 0.18 ± 0.05 |
| WZ42 pin | 14 weeks | 177.8 ± 47.1 | 65.6 ± 8.7 | 183.8 ± 33.3 | 0.20 ± 0.00 |
| Ti6Al4V pin | 14 weeks | 229.5 ± 198.5 | 56.8 ± 15.8 | 187.0 ± 33.5 | 0.18 ± 0.04 |
| WZ42 cuff | 14 weeks | 123.6 ± 36.3 | 64.0 ± 7.7 | 155.2 ± 21.7 | 0.20 ± 0.00 |
| Ti6Al4V cuff | 14 weeks | 154.4 ± 53.6 | 50.2 ± 3.4 | 163.6 ± 30.3 | 0.18 ± 0.04 |

| | Name | | | | | |
|---|---|---|---|---|---|---|
| | Total Protein | Albumin | Urea N | Creatinine | Globulin | |
| | | | Units | | | |
| | g/dL | g/dL | mg/dL | mg/dL | g/Dl | |
| | | | Ref. ranges | | | |
| | (5.8-7.1) | (3.2-3.7) | (13-19) | (0.3-0.5) | (2.6-3.5) | A/G Ratio |
| Unoperated | 5.7 ± 0.1 | 3.3 ± 0.1 | 20.7 ± 1.9 | 0.37 ± 0.08 | 2.4 ± 0.1 | 1.4 ± 0.1 |
| WZ42 pin | 6.3 ± 0.3 | 3.3 ± 0.2 | 20.3 ± 5.6 | 0.50 ± 0.00 | 3.0 ± 0.1 | 1.1 ± 0.1 |
| Ti6Al4V pin | 6.2 ± 0.1 | 3.3 ± 0.1 | 17.6 ± 2.1 | 0.42 ± 0.04 | 2.9 ± 0.2 | 1.1 ± 0.1 |
| WZ42 pin | 6.4 ± 0.3 | 3.5 ± 0.1 | 23.6 ± 2.1 | 0.52 ± 0.08 | 2.9 ± 0.3 | 1.2 ± 0.1 |
| Ti6Al4V pin | 6.4 ± 0.3 | 3.7 ± 0.2 | 21.8 ± 2.9 | 0.53 ± 0.05 | 2.7 ± 0.1 | 1.3 ± 0.1 |
| WZ42 pin | 6.4 ± 0.1 | 3.6 ± 0.1 | 22.2 ± 1.6 | 0.56 ± 0.05 | 2.7 ± 0.1 | 1.3 ± 0.1 |
| Ti6Al4V pin | 6.3 ± 0.3 | 3.7 ± 0.2 | 21.8 ± 2.5 | 0.52 ± 0.04 | 2.6 ± 0.2 | 1.4 ± 0.1 |
| WZ42 cuff | 6.3 ± 0.3 | 3.7 ± 0.2 | 24.8 ± 2.2 | 0.58 ± 0.04 | 2.6 ± 0.2 | 1.4 ± 0.1 |
| Ti6Al4V cuff | 6.2 ± 0.3 | 3.6 ± 0.1 | 19.6 ± 1.9 | 0.52 ± 0.04 | 2.6 ± 0.2 | 1.4 ± 0.1 |

Similarly, serum biochemical parameters are shown in Table 3, with kidney function measured by creatinine and urea levels, and liver function measured by the albumin, alkaline phosphatase, bilirubin, and glucose. All the parameters measured remained within the reference ranges or near pre-operation levels, demonstrating little effect of the implanted alloy materials on the kidney and liver function as well as the metabolism.

Electrolyte parameters calcium, sodium, chloride, phosphorous, and magnesium were measured from the serum samples which are shown in Table 4.

TABLE 4

Average values of electrolyte parameters of naive animals and animals implanted with WZ42 and Ti6Al4V alloy pins and cuffs at 2, 8, and 14 weeks after implantation.

| | | Name | | | | |
|---|---|---|---|---|---|---|
| | | Calcium | Sodium | Chloride | Phosphorous | Magnesium |
| | | | | Units | | |
| | Implantation | mg/dL | mmol/L | mmol/L | mg/dL | mg/dL |
| | | | | Ref. ranges | | |
| | time | (9.5-13.9) | (146-151) | (98-104) | (5.6-16.8) | (3.8-5.5) |
| Naïve | | 9.8 ± 0.2 | 138.2 ± 1.9 | 100.5 ± 1.0 | 5.5 ± 0.2 | 2.0 ± 0.2 |
| WZ42 pin | 2 weeks | 11.2 ± 0.1 | 144.8 ± 1.7 | 101.0 ± 1.4 | 8.5 ± 0.9 | 2.9 ± 0.3 |
| Ti6Al4V pin | 2 weeks | 11.5 ± 0.5 | 143.8 ± 1.6 | 100.2 ± 2.2 | 9.7 ± 1.9 | 3.4 ± 0.4 |
| WZ42 pin | 8 weeks | 11.6 ± 0.5 | 144.4 ± 1.9 | 100.6 ± 2.8 | 9.7 ± 1.4 | 3.5 ± 0.5 |
| Ti6Al4V pin | 8 weeks | 11.8 ± 0.6 | 146.5 ± 1.0 | 100.0 ± 1.4 | 11.3 ± 0.8 | 3.9 ± 0.4 |
| WZ42 pin | 14 weeks | 11.4 ± 0.3 | 147.8 ± 1.9 | 100.2 ± 2.0 | 9.8 ± 0.7 | 3.6 ± 0.2 |
| Ti6Al4V pin | 14 weeks | 12.2 ± 1.1 | 145.2 ± 2.6 | 99.0 ± 2.0 | 9.6 ± 1.2 | 3.6 ± 0.6 |

TABLE 4-continued

Average values of electrolyte parameters of naive animals and animals implanted
with WZ42 and Ti6Al4V alloy pins and cuffs at 2, 8, and 14 weeks after implantation.

| | | Name | | | | |
|---|---|---|---|---|---|---|
| | | Calcium | Sodium | Chloride | Phosphorous | Magnesium |
| | | | | Units | | |
| | Implantation | mg/dL | mmol/L | mmol/L Ref. ranges | mg/dL | mg/dL |
| | time | (9.5-13.9) | (146-151) | (98-104) | (5.6-16.8) | (3.8-5.5) |
| WZ42 cuff | 14 weeks | 11.3 ± 0.2 | 147.0 ± 0.7 | 101.4 ± 0.9 | 9.1 ± 1.4 | 3.2 ± 0.2 |
| Ti6Al4V cuff | 14 weeks | 11.6 ± 0.3 | 147.6 ± 1.1 | 99.6 ± 1.7 | 9.2 ± 0.7 | 3.3 ± 0.2 |

Magnesium levels remained in the low end of the reference ranges indicating no accumulation of degrading Mg from the implants in the collected blood. All the other electrolytes similarly remained consistent with levels of naïve rats and the prescribed allowable reference ranges.

ICP-OES results of the acid-digested liver and kidney demonstrated no accumulation of Mg exceeding the normal levels seen in the naïve control rats in the collected liver and kidney tissue in the WZ42 or Ti6Al4V groups. Ca and Zn concentration in the liver and kidney also did not deviate from the normal levels. Some differences were observed between the various groups, however, no significantly higher levels in the WZ42 groups of Mg, Ca, or Zn compared to naïve controls were observed. The concentration of other alloying elements (Y and Zr) measured from the digested liver and kidney were also perceived to be too low to be differentiated from normal levels, with Y being present in <0.7 µg/g dry mass in both liver and kidney, and Zr present in <2.2 µg dry mass in both liver and kidney.

Histological Examination of Liver and Kidneys

Figure 2:
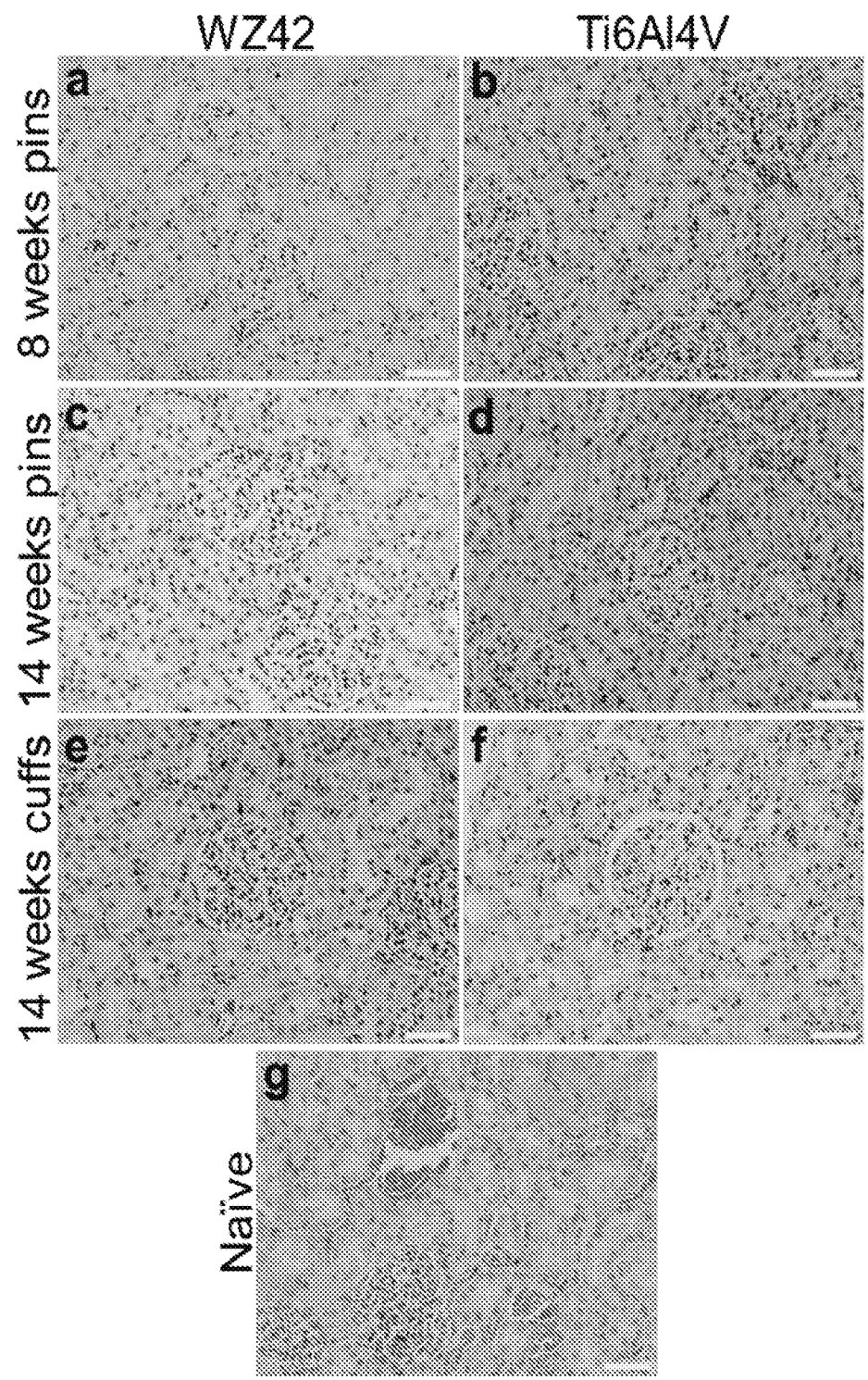
FIG. 2 is a plurality of photomicrographs of H&E stained kidneys of rats with femurs fixed by pins of WZ42 (a,c) and Ti6Al4V (b,d) after 8 weeks (a,b) and 14 weeks (c,d), stained images of kidneys from rats with implanted wire cuffs WZ42 (e) and Ti6Al4V (f) wrapped around bone for 14 weeks, and (g) of a naïve rat, in accordance with certain embodiments of the invention.

Conventional light microscopy images (FIG. 2 for kidney and FIG. 3 for liver) revealed that the cellular structure of the liver and kidney did not undergo any noticeable morphological changes or infiltration by inflammatory cells. No signs of obvious abnormalities were also observed in any of the organs sections.

Figure 4:
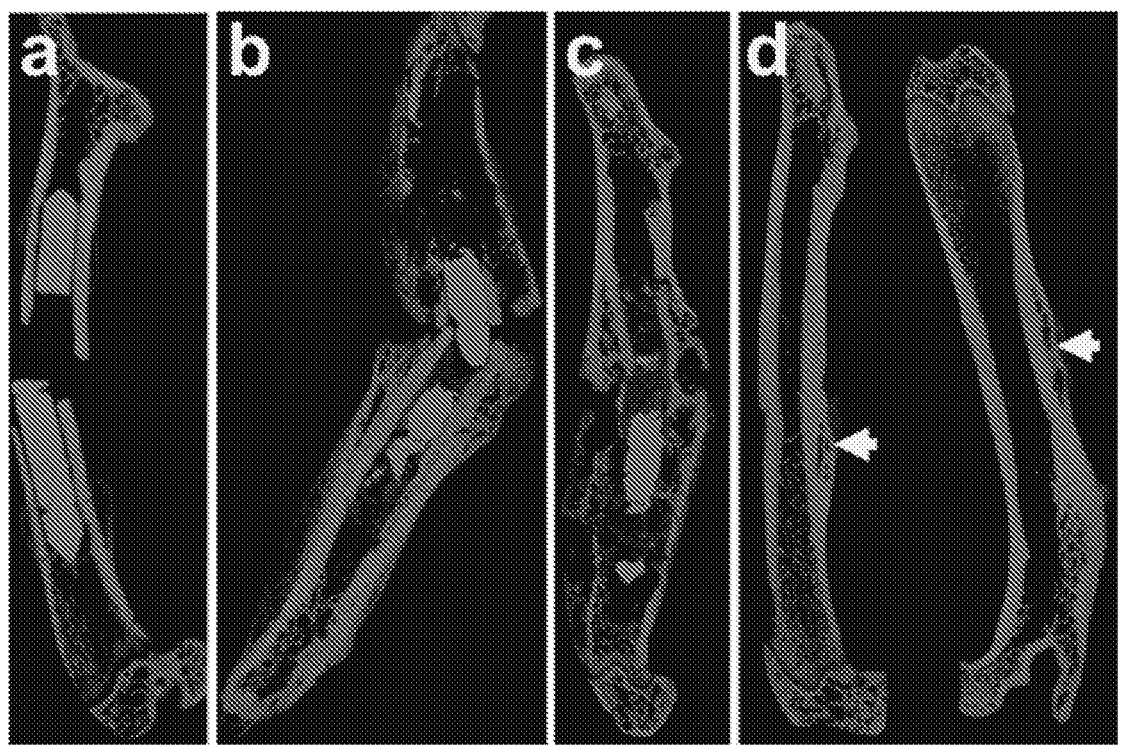
FIG. 4 is a plurality of micro-CT scans based on density thresholding with representative cross-sectional slices shown after implantation times of (a) 2 weeks, (b) 8 weeks, and (c) 14 weeks, wherein cuffs were fully degraded after 14 weeks (d) but new bone formation was seen in the region the wires occupied (arrows), in accordance with certain embodiments of the invention.

In Vivo Corrosion of Mg—Y—Zn—Zr—Ca Alloy Pins and Morphology of Surrounding Bone Representative cross-sectional micro-CT slices obtained from the femur-implant complex are shown in FIG. 4.

After two weeks of implantation, all the implanted pins had broken as seen in FIG. 4a, despite all pins appearing to be intact after 1 week as observed by X-ray (FIG. 1). These pin failures occurred near the site of the femoral fracture, resulting in mal-union. In addition, sites of pits of corrosion appeared at the junctions where the pins were clamped in collets during lathe machining as seen in FIG. 4a. Both of these two regions where the corrosion/failure occurred corresponded with regions of likely higher stress. Progressive degradation throughout the pins was observed at 8 and 14 weeks (FIGS. 4b and c). Regions of the pin surrounded by the cortical bone appeared to degrade more slowly. Micro-CT scans of intact femurs with WZ42 wire cuffs wrapped around the midsection of the diaphysis (FIG. 4d) revealed what appeared to be new bone formation in the region surrounding the degrading cuffs indicated by arrows, despite the cuffs having completely degraded after 14 weeks when the scans were performed.

Figure 5:
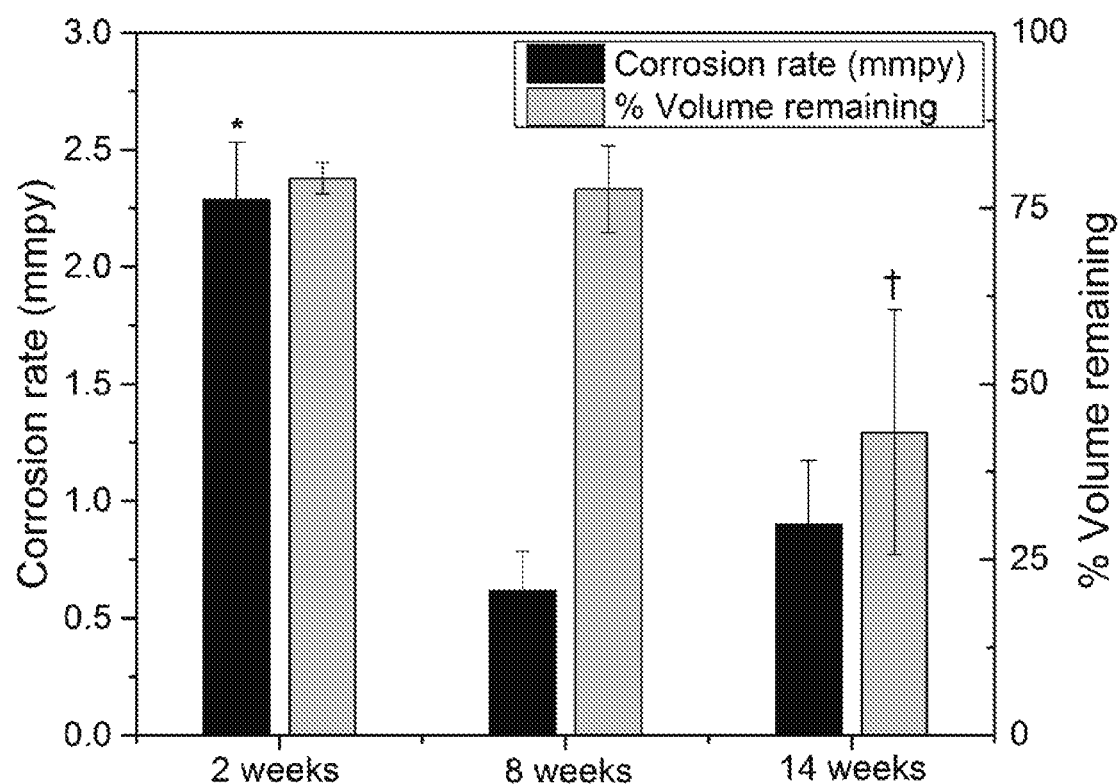
FIG. 5 is a bar graph that shows corrosion rate and % volume remaining of WZ42 pins implanted into rat femurs for 2, 8, and 14 weeks, wherein n≥2 for each group at each time point, * and † represent significant difference (p<0.05) compared to measurements made at other time points, in accordance with certain embodiments of the invention.

Following segmentation of the remaining WZ42 pins from the surrounding degraded product and bone, 3D reconstructions of the pins were created from which the volume was calculated. This remaining volume was used to calculate the corrosion rate at the end of 2, 8, and 14 weeks as shown in FIG. 5.

Degradation was found to occur more rapidly initially at 2 weeks, after which the corrosion rate was reduced and stabilized as seen by the lower corrosion rates calculated for 8 and 14 weeks. After the final time point of 14 weeks, approximately 43% of the original alloy pin volume remained.

Local Tissue Response to Mg—Y—Zn—Zr—Ca Alloy Pin

Figure 6:
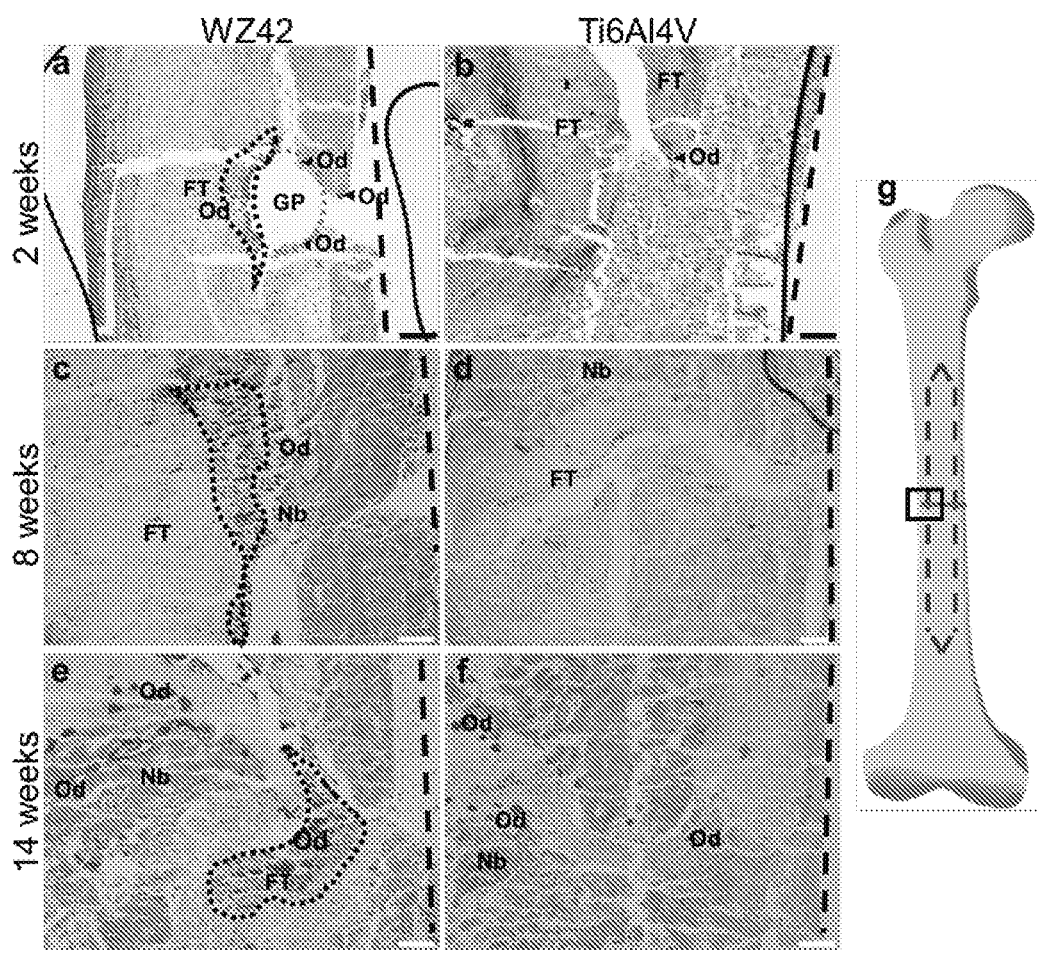
FIG. 6 is a plurality of photomicrographs of Goldner's Trichrome stained sections (40×) of soft and hard tissue at the femoral defect site fixed by pins of WZ42 magnesium alloy (a, c, e) and Ti6Al4V (b, d, f) after 2 weeks (a, b), 8 weeks (c, d), and 14 weeks (e, f) of implantation, (g) representation of region of interest imaged along longitudinal plane at defect site, in accordance with certain embodiments of the invention.

Femur explants were collected after 2, 8, and 14 weeks to assess the local tissue response to the WZ42 pins and cuffs and observe fracture healing. Sections of the bone from femurs containing the pins were stained using the Goldner's Trichrome method and are shown in FIG. 6.

After 2 weeks, in rats implanted with the WZ42 alloy intramedullary pins, dead spaces were observed over the fracture site in the fibrous tissue ("soft callus") that had formed around the bone. This was likely due to accumulation of hydrogen gas forming gas pockets (GP) from the degrading magnesium alloy as this was not observed in rats implanted with the Ti6Al4V pins. Osteoids (Od) had formed near the osteotomy region with fibrous tissue (Ft) surrounding the fracture site. After 8 weeks, the empty pocket over the fracture site was not perceived to be as prominent, potentially due to a slowing of the corrosion rate as measured by micro-CT (FIG. 5), dissipation of gas, and ingrowth of fibrous tissue. A greater presence of osteoids as well as new bone formation (Nb) in the periosteal region was observed progressively at 8 and 14 weeks. At 14 weeks' post-implantation, the fracture was not completely healed when fixed with either WZ42 or Ti6Al4V pins with narrow gaps remaining between the fragments of cortical bone not yet filled by mature cortical bone.

Alkaline phosphatase staining was conducted to observe osteoblast activity and the process of new bone formation in the region surrounding the defect. Osteoblast activity was more abundant surrounding the fracture in the femurs containing WZ42 at 8 and 14 weeks (FIG. 7c, e) compared to the femurs containing Ti6Al4V (FIG. 7d, f). The presence of osteoblasts appeared to peak at 8 weeks for the WZ42 group.

Figure 8:
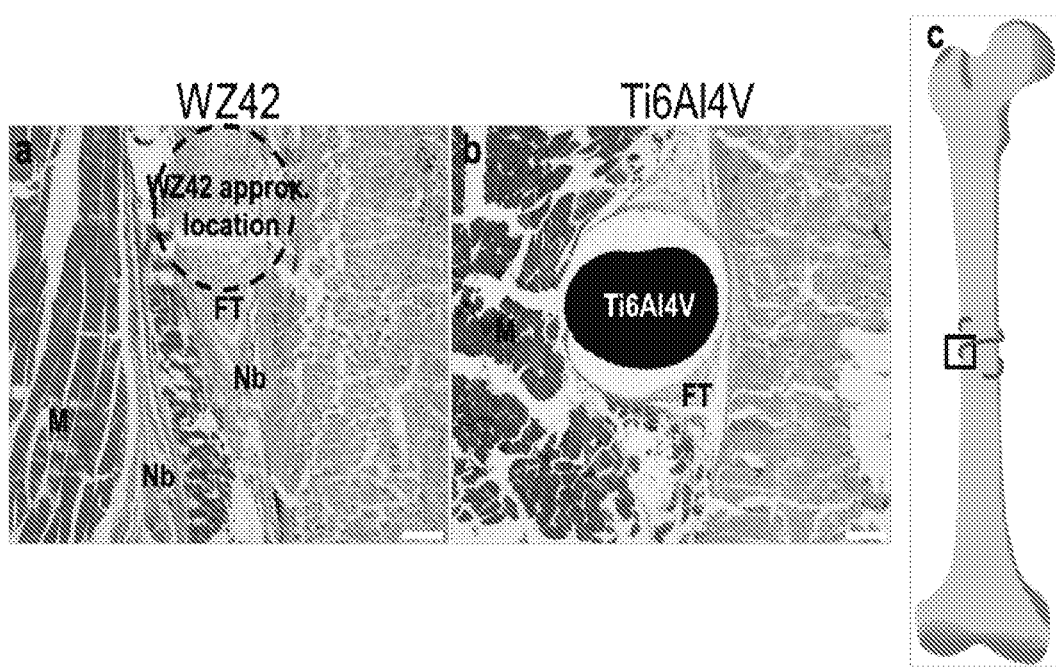
FIG. 8 is a plurality of photomicrographs of Goldner's Trichrome stained sections (40×) of soft and hard tissue at the implant-bone interface where wire cuffs of WZ42 magnesium alloy (a) and Ti6Al4V (b) were wrapped around bone for 14 weeks of implantation (c) representation of region of interest imaged along longitudinal plane at defect site, in accordance with certain embodiments of the invention.

Goldner's Trichrome stained sections of tissue near the site of wire cuff implantation (FIG. 8) displayed new bone as seen in light blue-green as well as fibrous tissue in the region surrounding the Mg alloy cuff implant (FIG. 8a). In contrast, new bone formation was not seen around the inert Ti6Al4V cuff (FIG. 8b).

Discussion

The example described herein illustrates the response of WZ42 magnesium alloy when tested in a challenging orthopedic model prone to considerable stress corrosion, while at the same time demonstrating its biocompatibility without eliciting any toxicity. Moreover, the WZ42 alloy induced new bone formation and bone healing surrounding a fractured femur. The main animal model was a closed femoral fracture stabilized by an intramedullary pin. An evaluation of permanent metal pins for bone healing and mineralization was conducted. Despite these instances of permanent metals, such as stainless steel or Ni—Ti alloys being used to fix full osteotomies in rats, such an aggressive model representing the existence of and exposure to large dynamic stresses that will likely accelerate corrosion, has not been tested with magnesium alloys particularly, with the aim of assessing the toxicity and biocompatibility. The example also confirmed the safety of Mg in this challenging model and analyzed the degradation behavior as a result of the high stress being placed on the Mg pins.

To assess the safety of the WZ42 implants, biochemical analysis of the blood and serum was conducted. The lower than expected platelet levels for the WZ42 and Ti6Al4V pin groups at 14 weeks, and WZ42 wire cuff group also at 14 weeks, was likely due to platelet clumping in samples, which was reported in many samples analyzed. The slightly elevated levels of white blood cells 2 weeks after surgeries for WZ42, as well as Ti6Al4V, represents a common post-surgical inflammatory response known to occur during wound healing, which returned to normal levels in a follow-up evaluation. This was paralleled by no clinical sign of any surgical site infection. The consistent electrolyte levels as measured in blood and the stable Mg concentration measured in the digested kidney and liver signifies that the degradation of WZ42 did not cause any disturbances in the balance of physiological electrolyte levels. Along with the unaltered serum biochemical parameters, it was suggested that liver and kidney functions were not affected by the WZ42 alloy degradation, concentrations of Mg, Ca, and Zn (elements contained in the WZ42 alloy) in the liver and kidney did not rise above levels measured in naïve rats. Concentrations were also consistent with rats implanted with Ti6Al4V samples compared at the same time points.

To further demonstrate systemic biocompatibility, H&E staining of liver and kidney samples did not reveal any signs of organ alteration or damage. No focal mineralization, acute inflammatory cell infiltration, or necrosis were observed in kidney tissues. In the liver, no aggregates of inflammatory cells or features of hepatocellular necrosis such as irregular patchy areas of coagulation necrosis were observed. These results suggest that the WZ42 alloy and its degradation products are systemically biocompatible.

Progressive degradation was observed in the intramedullary WZ42 pins as seen in the reducing cross sectional area of the implants seen in FIG. 4(a-c), and calculated corrosion rate and volume loss shown in FIG. 5. Degradation appeared to occur preferentially at the fracture site, perpendicular to the fracture, where the stresses acting on the implanted pin are expected to be the highest. This synergy of mechanical loading combined with the corrosive environment of surrounding fluids in the body has been shown to cause sudden fracture of implants via the stress corrosion cracking (SCC) mechanism. This embrittlement phenomenon may occur even when the applied stress does not exceed the yield strength of the material, reducing the time to fracture and causing premature brittle failure. Magnesium, suffering from pitting corrosion, a source from which SCC can develop, has shown susceptibility to SCC in chloride solutions and simulated body fluids. Other localized regions of corrosion, such as near the end of the pin in FIG. 4a, occurred due to pre-existing flaws imparted during lathe machining, which increased the susceptibility to SCC. Degradation at the site of fracture was also promoted by the higher exposure to the surrounding fluid electrolyte due to small gaps between the two sides of the femur, acting to produce fluid shear stress and remove local $OH^-$ ions to reduce the protection that arises from the passivation layer. During the early stages of healing after implantation when inflammatory responses were occurring, the characteristic hypoxic and acidic environment optimal for activities of polymorphonuclear leukocytes and tissue macrophages also resulted in higher corrosion rate due to magnesium hydroxide's instability in acidic conditions and infiltration of these cells at the site of fracture causing phagocytosis of the metal debris. After this initial inflammatory phase and more rapid corrosion rate at 2 weeks, corrosion slowed when measured after 8 weeks as the surface of the Mg implant became further passivated and the fracture site enclosed in fibrous tissue, soft callus, and eventually newly formed bone. During the bone repair progression, the pH had risen ultimately becoming slightly alkaline to optimize alkaline phosphatase activity to perform its role in callus mineralization, thereby becoming more conducive to the formation of the passivating magnesium hydroxide layer on the surface of the degrading WZ42 pins. The percentage volume remaining did not significantly change between 2 and 8 weeks because the measurements were taken from different samples at each time point. For the implants used to calculate the 8 week measurements, the corrosion rate was lower such that over time, the volume remaining was not significantly different from the samples measured after 2 weeks, which degraded at a much faster rate. The variation between samples that caused the difference in degradation for 2 versus 8 week samples may be due to variability in when the pins failed, or pins not being fully surrounded by cortical bone due to mal-union and thus, being exposed to more surrounding fluid leading to enhanced corrosion. The thin WZ42 wires wrapped around the outside of the femur, while being visually apparent in X-ray after 1 week (FIG. 1d), were completely degraded after 14 weeks as seen in FIG. 4d as a result of their smaller profile as well as being exposed to a much more corrosive environment having been placed on the surface of the femur instead of being surrounded by the cortical bone.

The effect of the degrading Mg alloy on the surrounding tissue was investigated via Goldner's Trichrome and ALP staining after 2, 8, and 14 weeks' post-implantation of the WZ42 and Ti6Al4V intramedullary pins and extra-cortical cuffs. After 2 weeks in rats implanted with the WZ42 alloy (FIG. 1a, FIG. 6a), gas pockets (GP) were observed over the fracture site forming empty cavities in the surrounding in fibrous tissue. This was likely due to accumulation of hydrogen gas from the degrading magnesium alloy, as this is not observed in the Ti6Al4V pins. Despite potential concerns of the effects of these gas pockets on the healing processes, no bone erosion due to these cavities was observed in rabbits after 1 year follow-up assessment of another Mg alloy also containing Mg, Y, and Zr similar in composition to the WZ42 alloy used herein. After 8 weeks (FIG. 6c), the gas pocket over the fracture site fixed with WZ42 was not as prominent, potentially due to slowing of corrosion rate, absorption of gas, and ingrowth of fibrous tissue. Clinical implantation of Mg alloy screws also revealed hydrogen gas formation soon after implantation, which disappeared through absorption into surrounding tissue by approximately 2-4 weeks post-surgery. Despite the appearance of hydrogen gas, formation of calcification matrix was not inhibited to initiate the bone formation process, allowing for success in the long-term clinical study.

Figure 7:
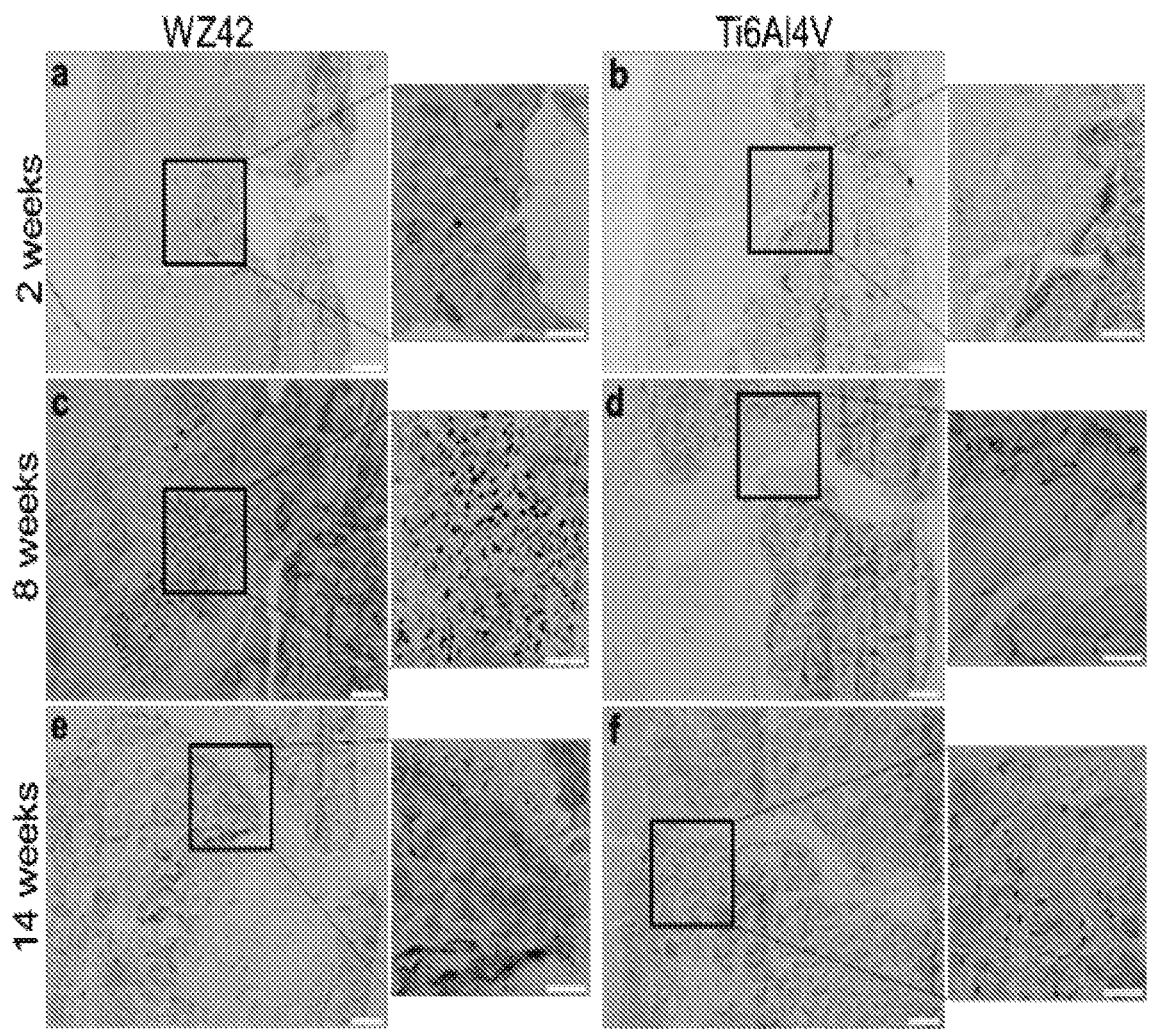
FIG. 7 is a plurality of photomicrographs of the localization of ALP at 40× and 100× (inset) of tissue at the femoral defect site fixed by pins of WZ42 magnesium alloy (a, c, e) and Ti6Al4V (b, d, f) after 2 weeks (a,b), 8 weeks (c,d), and 14 weeks (e,f) of implantation, in accordance with certain embodiments of the invention.

The bone healing process of the fractured rat femurs consisted of several phases as observed using staining at various time points. After two weeks, the inflammatory phase of fracture healing appeared to have passed, with bone healing entering the reparative phase characterized by the development of callus tissue forming in and around the fracture site to be later replaced by bone. The presence of osteoids (Od) was observed near the bone with fibrous tissue (Ft) to indicate the initial composition of the soft callus surrounding the fracture site. A greater presence of osteoids, as well as new bone formation (Nb) in the periosteal region, was observed progressively after 8 and 14 weeks. After 14 weeks, the fracture was not yet completely healed with full woven bone when fixed with either WZ42 (FIG. 6e) or Ti6Al4V (FIG. 6f) pins. However, the presence of mineralized tissue indicated callus calcification as the mineralization process progressed. The elevated new bone formation seen in the WZ42 group at 8 and 14 weeks, which was further confirmed by ALP staining (FIG. 7). ALP is necessary for mineralization of the callus providing phosphate ions for precipitation with calcium. Osteoblast activity as indicated by ALP staining demonstrated promotion of new bone formation in the region surrounding the defect at the leading edge to heal the fracture. ALP activity peaked at 8 weeks for the WZ42 group with higher activity compared to the Ti6Al4V group. Despite the fracture not having healed fully due to the instability of the intramedullary fixation, the healing process appeared to be un-encumbered. In fact, the prevalence of new bone formation as seen in the mineralized new bone and osteoblast activity in regions adjacent to the Mg alloy implants, confirmed results of studies reporting enhanced new bone formation around Mg-based implants related to the cellular activity of Mg such as osteoconductivity of the phosphate layer forming on the surface of magnesium-based implants, and promotion of enhanced mineralization from bone marrow stromal cells. Additionally, the consistent observations of a normal healing response of a fibrous capsule enclosing the operation site with no abnormal presence of inflammatory cells at the implant site, has been observed. Mg scaffolds show good biocompatibility that is indicative of the local biosafety of the Mg alloy. Without a defect created in the case of the wire cuff placed over the cortical bone, the phenomenon of enhanced new bone formation was confirmed in the region surrounding the Mg alloy cuff implant compared to the inert Ti6Al4V (FIG. 8).

Overall, the positive biocompatibility and signs of healing with new bone formation observed suggest that the WZ42 alloy is a suitable candidate for orthopedic applications provided care is exhibited to limit the mechanical stresses placed on the implant, and that a consistent finish on the alloy is obtained by careful machining so as to reduce the onset of rapid corrosion and potential failure brought on by stress corrosion cracking. Immobilization of the fracture following implantation of the pins can serve to alleviate the direct exposure of the implants to the extreme dynamic stresses leading to accelerated corrosion. The model tested here provided an ideal environment contributing to creating a high dynamic stress on the implant site. Thus, loading the femur and completely transferring this load directly onto the Mg intramedullary pin leading to a highly aggressive load and corrosion condition causing the pins to ultimately fail. The dynamic nature of the stresses combined with aggressive movement fostered by ambulation of the animals lead to variation in the progression of the corrosion. As a result, variability in the non-union and healing could be seen (FIG. 4a, 4b). This aggressive loading model showed that, despite having such an aggressive condition that could be perceived as an extreme event along with accelerated corrosion, local and systemic biocompatibility of the alloy was still observed. Despite the initial higher corrosion rate, hydrogen gas formation was fairly limited and not externally noticeable, while the surrounding tissue response, kidney and liver, and blood parameters all remained normal. Thus, alluding to the safety of these alloys. With temporary unloading and immobilization, as is the standard of treatment for orthopedic injuries, the risk of failure of the WZ42 alloy would likely be diminished, still rendering the alloy as a suitable orthopedic implant material, with potential success in other medical device applications. Semi or non-load bearing environments placed on orthopedic Mg implants demonstrate the safety and efficacy of the implants. The model implemented without any harness demonstrates the safety and non-toxicity of Mg, and the alloying elements used to process the alloy to the extent of the size and dimensions used compared to the rats employed.

Conclusions

WZ42 (Mg—Y—Zn—Zr—Ca) alloy pins were implanted into the intramedullary cavity of fractured rat femurs and as wires wrapped around the midsection of un-altered femurs, comparing the Mg alloy to Ti6Al4V. Degradation of the intramedullary pins led to failure due to perceived stress related corrosion initiated at the osteotomy site of high mechanical loading and surrounding vasculature aiding corrosion. However, the WZ42 alloy was found to be biocompatible with no recognizable accumulation of Mg or alloying elements in the blood, liver, or kidney, and no adverse effects on blood count, or metabolic, kidney, and liver function. Histology of the local area at the implant site showed normal fracture healing and new bone formation. These positive results, despite the challenging nature of the model, indicated the suitability of this alloy, WZ42, for orthopedic fixation applications.

Example 2

This example evaluates the degradation effects, local tissue response, and systemic toxicity of Mg-4Zn-0.1Sr-0.5Zr pins implanted in the intramedullary region of fractured rat femurs. Mg alloys are not intended for use as femoral rods. However, a rat femoral fracture model was selected to primarily assess the degradation profile of Mg—Zn pins and demonstrate the toxicity of Mg—Zn pins under load-bearing conditions.

Materials and Methods

Alloy Processing and Femoral Pin Fabrication

Mg-4Zn-0.1Sr-0.5Zr (Mg—Zn) alloy was synthesized using an electrical resistance furnace (Wenesco Inc.). Pure Mg (US magnesium Inc. 99.97%), Zn shots (Alfa-Aesar 99.99%), and Mg-30Sr master alloy were melted in a mild steel crucible. The total melt amount was 250 g. The melting process was performed using 0.5% SF6 plus balance Ar protective gas atmosphere to protect the molten magnesium alloy from oxygen. The molten mixture of Mg, Zn, and Sr was homogenized at 700° C. and the zirconium content was added using Zirmax® (Mg-33.3 wt % Zr) master alloy (Magnesium Elektron Ltd.). After 1 and 5 minutes, the liquid melt was further homogenized by stirring for 10 seconds to dissolve and disperse the zirconium particles uniformly. The melt was maintained at 700° C. for 30 minutes and following, the molten liquid was poured into a mild steel mold (44.5 mm×82.5 mm) preheated at 500° C.

The middle part of the as-cast Mg—Zn—Sr—Zr (Mg—Zn) alloy following removal of the top, sides and the bottom, was machined to a dimension of 37.6 mm diameter and 60 mm height by using a lathe. The as-cast Mg—Zn—Sr—Zr (Mg—Zn) alloy was then heat-treated at 300° C. for 1 hour, quenched in oil, and annealed at 205° C. for 12 hours. Following heat treatment, hot extrusion was performed using an extrusion ratio of 30:1 at North Carolina A&T University (Greensboro, N.C.).

Animal Study Design

An animal study was conducted in accordance with a protocol approved by Animal Care and Use Committee (IACUC) at the University of Pittsburgh. Groups, time points, and number of animals involved in the current chapter are identified in Table 1A.

TABLE 1A

Groups, time points, and number of animals used for Ti and Mg—Zn device implantation.

| Group | Time point | N/time point |
|---|---|---|
| Ti alloy pins | 2 and 14 weeks | 5 |
| Mg—Zn pins | 2 and 14 weeks | 5 |
| Ti alloy cuffs | 14 weeks | 5 |
| Mg—Zn cuffs | 14 weeks | 5 |

Thirty, Sprague-Dawley rats of approximately 250 g of body weight were used. Fifteen rats were randomly selected for Ti alloy implantation and the other rats were implanted with Mg alloy pins. For each implant material, ten rats were implanted with pins for 2 and 14 weeks and five rats were implanted with the cuff for 14 weeks. For each pin implanted, the right femur of each rat was approached laterally and an osteotomy was performed in the middle of the femur using a dremel drill with a diamond wheel blade. A pin of Ti or Mg alloy was inserted into the intramedullary region to achieve a stable reunion of the fractured femur. Five rats from both Ti and Mg groups were sacrificed for fracture healing and toxicity analysis after 2 or 14 weeks of implantation. For each cuff implantation, a cuff of Ti or Mg—Zn alloy was implanted around the unfractured femur for toxicity analysis after 14 weeks.

Radiographic Imaging and Computer Tomography Analysis

X-ray images of all animals were obtained after 7 days to observe implant location and alignment of fractured femurs. The Mg—Zn alloy pins before implantation were scanned using micro-computed tomography (microCT) (VivaCT40; Scanco Medical, Switzerland). The harvested femurs were also scanned using microCT, after embedding in plastic. Analysis of the microCT images were performed using Mimics (Materialise, Belgium) to calculate the degradation rate of the Mg alloy pins and assess fracture healing. Averages and standard deviations of five sample measurements were reported and t-test was used to determine any significant mean differences with a p-value less than 0.05 for Mg—Zn pin groups at different time points.

Blood Test

Blood samples were obtained before operation and after euthanasia at 2 and 14 weeks. The samples collected in K2-EDTA were sent to Marchfield Labs (Cleveland, Ohio) for hematologic analysis. Red blood cell count, hemoglobin, hematocrit, platelet count, and white blood cell count were analyzed using a Sysmex XT2000i Automated Hematology Analyzer (Sysmex Corporation, Japan). For biochemical analysis, the blood samples were maintained at room temperature to clot for 30 minutes and centrifuged at 2,000 rpm for 10 minutes. The supernatant serum samples were analyzed using an Olympus AU chemistry analyzer (Olympus Corporation, Japan). Alanine aminotransferase (ALT), alkaline phosphatase (ALP), total protein, albumin, total and direct bilirubin, cholesterol, glucose, urea, creatinine, phosphorus, chloride, potassium, sodium, and magnesium were accordingly measured. Averages of three sample measurements were reported and compared to the reference ranges for each parameter.

ICP Analysis

Harvested liver and kidney tissues were dried in an oven at 70° C. overnight. Dried tissue samples were then ground using a mortar and pestle. 0.5 g of ground tissues were dissolved in 5 mL of concentrated nitric acid that was kept heated at 130° C. for 14 hours, and supplemented with 1 mL of 30% hydrogen peroxide. Sample solutions were then diluted 10 times and measured using an inductively coupled plasma optical emission spectroscopy (ICP-OES, iCAP duo 6500 Thermo Fisher, Waltham, Mass.), with standard solutions of the various elements being analyzed. Averages and standard deviations of three sample measurements were reported and one-way ANOVA was used to determine any significant mean differences with a p-value less than 0.05 for all other groups.

Soft Tissue Histology

Harvested liver and kidney tissues were fixed in 10% neutral buffered formalin for 48 hours. The fixed tissues were sectioned in small pieces, dehydrated in ethyl alcohol series from 70% to 100%, cleaned using xylene substitute and embedded in paraffin. Paraffin tissue blocks were then sectioned using a rotary microtome. Tissue slices were accordingly dewrinkled on a warm water bath, and transferred to glass slides. After drying, tissue slides were imaged using an optical microscope after staining with hematoxylin and eosin (dyes) and mounted using a mounting solution.

Bone Tissue Histology

Undecalcified embedding was used to perform histology analysis of the harvested femurs with implants. Harvested femurs were fixed in 70% ethyl alcohol for 72 hours. The fixed femurs were then dehydrated in diluted ethyl alcohol from 70% dilution to 100% consecutively. The femurs were cleaned in xylene and embedded in poly methyl methacrylate (PMMA) (OsteoBed, Life Technology). Then, 7 to 10 um tissue sections were obtained from the embedded femurs using a rotary microtome with a tungsten carbide blade. Sections were adhered to tape to prevent shattering during sectioning. Sections were subjected to Goldner's Masson Trichrome and alkaline phosphatase (ALP) staining. The stained sections were mounted on a glass slide using a glycerol solution and observed under an optical microscope.

Figure 9:
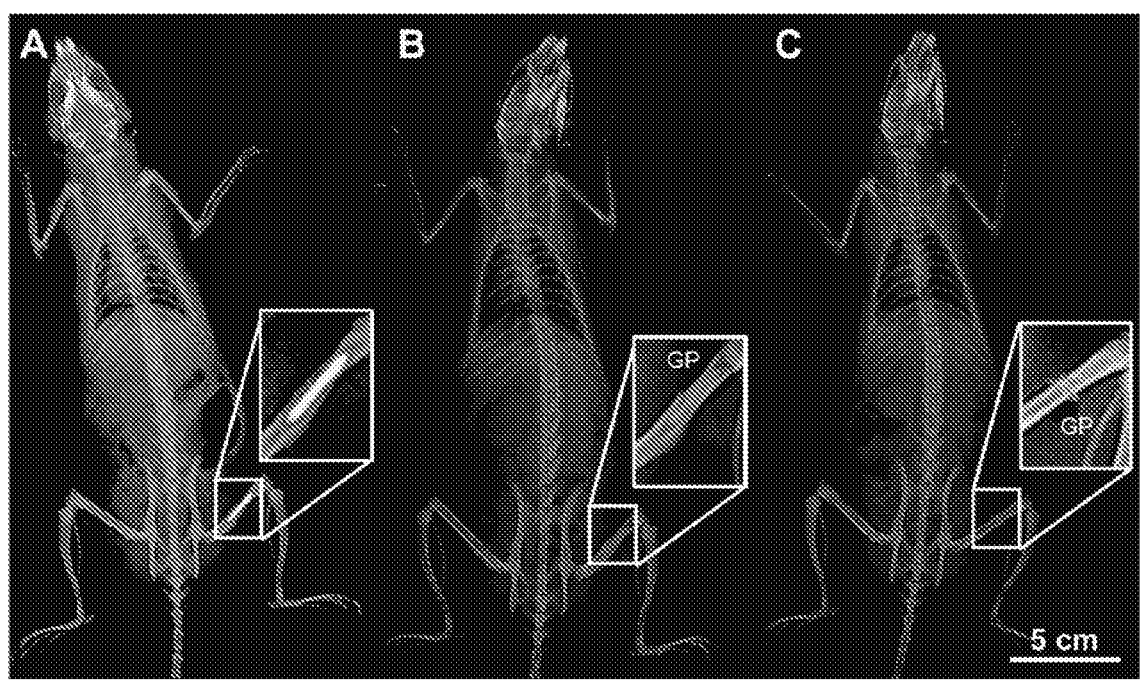
FIG. 9 is a plurality of x-ray radiograph images of (a) Ti pin, (b) Mg—Zn pin and (c) Mg—Zn cuff pin implanted in rats after one week (wherein GP is gas pocket), in accordance with certain embodiments of the invention.

Results
In Vivo Degradation of the Magnesium-Zinc-Zirconium-Strontium (Mg—Zn—Zr—Sr) Alloy Pins X-ray radiograph images of Ti and Mg—Zn pin-implanted rats after one week of osteotomy surgery, as shown in FIG. 9, were obtained to identify the position of Mg—Zn and Ti pins and fracture fixation stability. In the x-ray image, some visible hydrogen gas evolution was observed around the Mg—Zn implants as shown in FIGS. 9b and 9c. Rats implanted with both Ti and Mg—Zn pins exhibited normal movement and ambulatory behavior.

Harvested femurs exhibited normal fracture healing response with intramedullary pins. Callus formation was observed around the wound. Callus formed on the femurs with both Ti and Mg—Zn pins exhibited no visible difference. However, the callus formed on the femurs after 8 and 12 weeks of implantation was more hardened compared to the callus after 2 weeks of implantation. The fracture femurs with Mg—Zn pins was not aligned as straight as the femurs with Ti pins.

Figure 3:
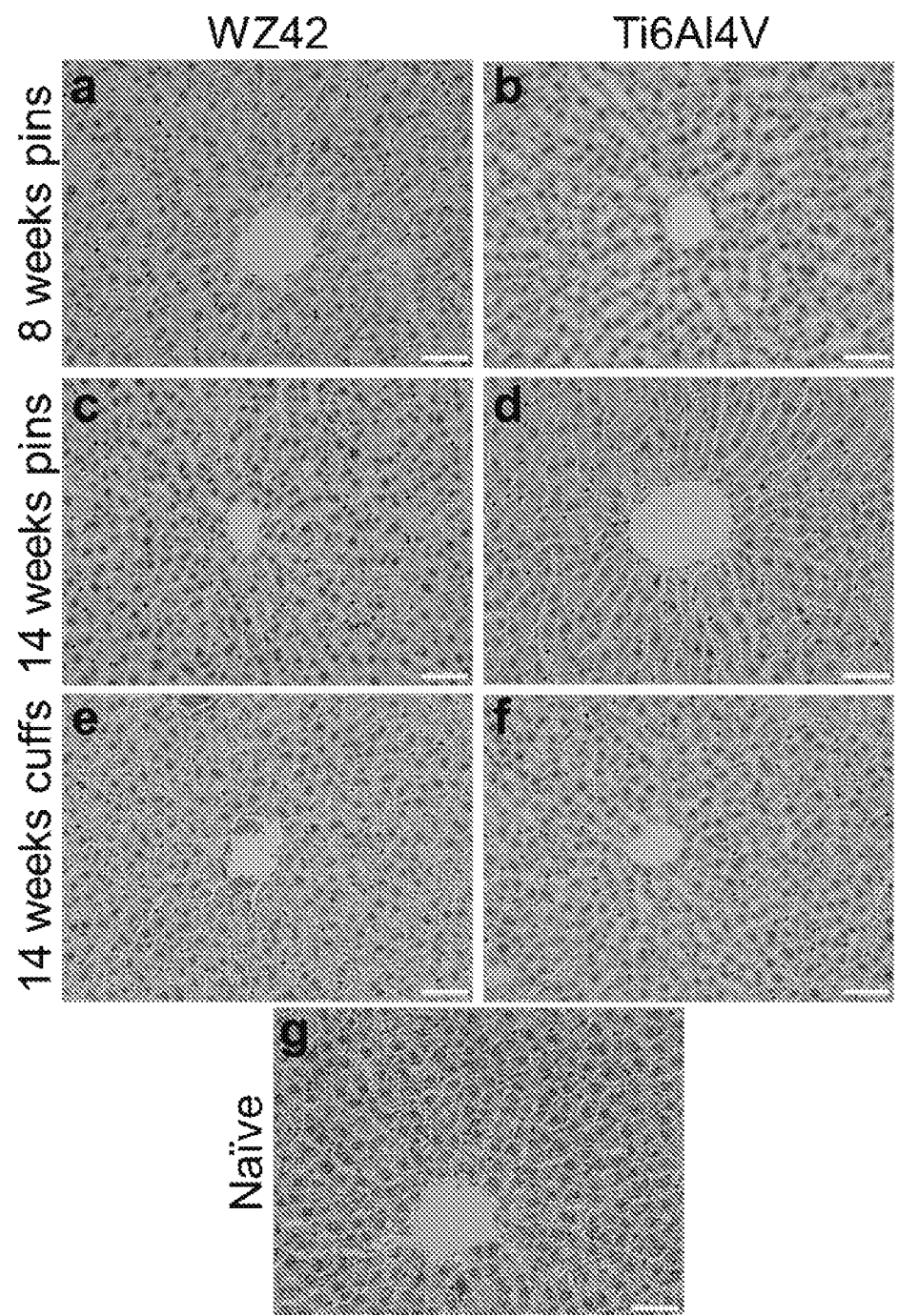
FIG. 3 is a plurality of photomicrographs of H&E stained livers of rats with femurs fixed by pins of WZ42 (a,c) and Ti6Al4V (b,d) after 8 weeks (a,b) and 14 weeks (c,d), stained images of kidneys from rats with implanted wire cuffs WZ42 (e) and Ti6Al4V (f) wrapped around bone for 14 weeks, and (g) of a naïve rat, in accordance with certain embodiments of the invention.
Figure 10:
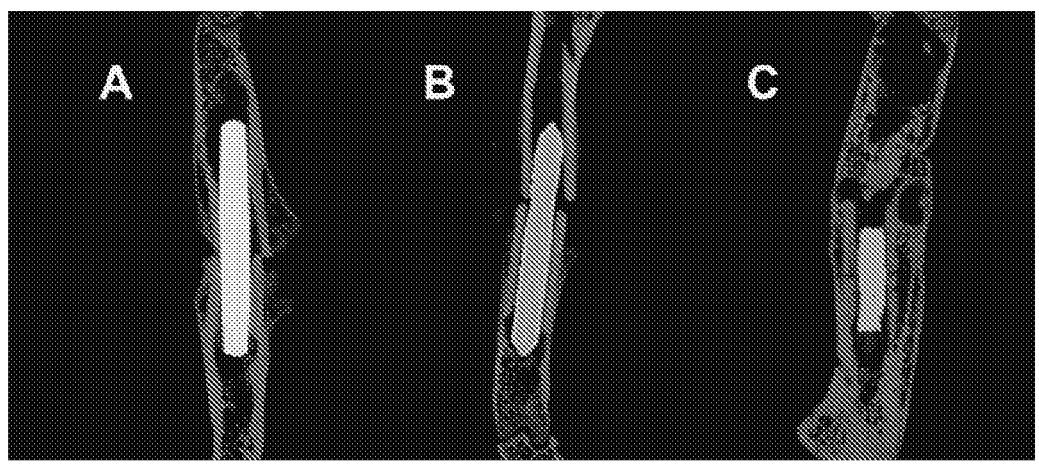
FIG. 10 is a plurality of micro CT analysis images of (a) Ti pin at 14 weeks, (b) Mg—Zn pin at 2 weeks, and (c) Mg—Zn pin at 14 weeks, in accordance with certain embodiments of the invention.

FIG. 10 shows the representative micro-computed tomography (micro-CT) images of rat femurs with Ti or Mg—Zn pins after plastic embedding. A femur with a broken Mg—Zn pin resulted in a misalignment of fractured bones. At 2 weeks, three out of five Mg—Zn pins were fractured into two pieces. The Ti pins, however, exhibited no fracture or damage due to the load. Mal-union of the femurs with broken Mg—Zn pins can lead to a significant difference in the fracture healing. The micro-Ct images at 14 months for both Ti and Mg—Zn pins implanted, as shown in FIG. 3, indicated that the fracture healing process was not completed. More hydrogen gas bubbles were evolved around Mg—Zn pins following 2 weeks of implantation not distinguishable in micro CT but was noticeable in the histology (later discussed herein). After 14 weeks, the gas bubbles were not distinguishable in the micro-CT images.

The remaining volume of Mg—Zn pins in the intramedullary region was analyzed from the micro-CT images. The remaining volume of Mg—Zn pins after 2 weeks of implantation was 87.7%. After 14 weeks, the remaining volume was significantly decreased to 42.0%. Corrosion rates of Mg—Zn pins were calculated from the volume loss and original surface area. Mg—Zn pins for 2 weeks of implantation exhibited the corrosion rate of 0.91±0.65 mmpy. The corrosion rate at 2 weeks was anticipated to be higher than the other time points since the Mg—Zn pins was exposed to the largest mechanical stress at the 2 weeks' time point. The Mg—Zn pins for 14 weeks of implantation continued to degrade with larger surface area being exposed which resulted in the corrosion rate of 0.77±0.30 mmpy.

Blood Test Results

Table 2A summarizes blood test results of rats before and after osteotomy surgeries for 2 and 14 weeks of Ti and Mg—Zn pins/cuffs implantation.

TABLE 2A

Hematologic analysis results from blood panel test after Ti pin (2 and 14 weeks), Mg—Zn pin (2 and 14 weeks), and Mg—Zn cuff (2 weeks) implantations.

| | Implantation time | Red Blood Cell Count $10^6$/uL | Hemoglobin g/dL | Platelet Count $10^3$/uL | White Blood Cell Count $10^3$/uL |
|---|---|---|---|---|---|
| Ref. ranges | | (7.00-9.00) | (13.7-16.8) | (680-1280) | (1.1-7.5) |
| Pre-operation | | 7.4 | 14.1 | 618.3 | 6.8 |
| Ti pin | 2 weeks | 7.8 | 14.9 | 656.0 | 9.0 |
| Mg—Zn pin | 2 weeks | 7.4 | 14.1 | 547.0 | 3.7 |
| Ti pin | 14 weeks | 7.5 | 14.0 | 563.0 | 5.9 |
| Mg—Zn pin | 14 weeks | 7.3 | 13.7 | 598.0 | 4.5 |
| Ti cuff | 14 weeks | 7.6 | 13.8 | 637.0 | 5.8 |
| Mg—Zn cuff | 14 weeks | 7.2 | 13.4 | 537.0 | 6.2 |

Red blood cell, hemoglobin, and platelet count exhibited no significant difference in the groups for the different implants and the different time durations. White blood cell count after 2 weeks of Ti pin implantation was significantly higher compared to the Mg—Zn group. However, it still remained within a reference range.

Biochemical analysis results rats before and after osteotomy surgeries for 2 and 14 weeks of Ti and Mg—Zn pins/cuffs implantation are listed in Table 3A.

ALT after 2 weeks of implantation for both Ti and Mg—Zn pins exhibited significantly higher level compared to the implants for the other time points. However, these ALT values still remain within a reference range. For ALP, TBIL, TP, ALB, UA, CR, and GLB, all groups exhibited no significant difference between implants and implantation duration suggesting no signs of liver or kidney damage due to degradation of Mg—Zn pins.

TABLE 3A

Biochemical analysis on blood serum after Ti pin (2 and 14 weeks), Mg—Zn pin (2 and 14 weeks), and Mg—Zn cuff (2 weeks) implantations.

| | | Name | | | | | | | | | |
|---|---|---|---|---|---|---|---|---|---|---|---|
| | | Glucose | ALT (GPT) | ALP | Total Bilirubin | Total Protein | Albumin | Urea N | Creatinine | Globulin | |
| | | mg/dL | U/L | U/L | mg/dL | g/dL | g/dL | mg/dL | mg/dL | g/Dl | |
| | | | | | | Units Ref. ranges | | | | | |
| | Implantation time | (70-308) | (59-166) | (232-632) | (0.0-0.1) | (5.8-7.1) | (3.2-3.7) | (13-19) | (0.3-0.5) | (2.6-3.5) | A/G Ratio |
| Unoperated | | 181.2 | 55.8 | 175.2 | 0.17 | 5.7 | 3.3 | 20.7 | 0.37 | 2.4 | 1.4 |
| Ti pin | 2 weeks | 322.0 | 132.6 | 151.2 | 0.14 | 6.2 | 3.3 | 17.6 | 0.42 | 2.9 | 1.1 |
| Mg—Zn pin | 2 weeks | 293.0 | 123.0 | 140.0 | 0.18 | 6.7 | 3.5 | 20.5 | 0.53 | 3.2 | 1.1 |
| Ti pin | 14 weeks | 229.5 | 56.8 | 187.0 | 0.18 | 6.3 | 3.7 | 21.8 | 0.52 | 2.6 | 1.4 |
| Mg—Zn pin | 14 weeks | 124.2 | 57.8 | 181.8 | 0.20 | 6.3 | 3.6 | 22.2 | 0.56 | 2.7 | 1.3 |
| Ti cuff | 14 weeks | 154.4 | 50.2 | 163.6 | 0.18 | 6.2 | 3.6 | 19.6 | 0.52 | 2.6 | 1.4 |
| Mg—Zn cuff | 14 weeks | 203.0 | 59.4 | 190.4 | 0.16 | 6.5 | 3.8 | 23.2 | 0.52 | 2.7 | 1.4 |

Calcium, sodium, chloride, phosphorous, and magnesium ion levels in the serum before and after implantation are listed in Table 4A. No significant difference in these ion levels were found between implants or implantation duration. All values remained within the reference range suggesting that there were no changes to the systemic ion concentration due to implantation and the consequent degradation of the Mg—Zn—Zr—Sr alloy pins.

TABLE 4A

Electrolyte levels of blood serum after Ti pin (2 and 14 weeks), Mg—Zn pin (2 and 14 weeks), and Mg—Zn cuff (2 weeks) implantations.

| | | Name | | | | |
|---|---|---|---|---|---|---|
| | | Calcium | Sodium | Chloride | Phosphorous | Magnesium |
| | | mg/dL | mmol/L | mmol/L | mg/dL | mg/dL |
| | | | | Units Ref. ranges | | |
| | Implantation time | (9.5-13.9) | (146-151) | (98-104) | (5.6-16.8) | (3.8-5.5) |
| Unoperated | | 9.8 | 138.2 | 100.5 | 5.5 | 2.0 |
| Ti pin | 2 weeks | 11.5 | 143.8 | 100.2 | 9.7 | 3.4 |
| Mg—Zn pin | 2 weeks | 12.1 | 141.3 | 100.3 | 12.0 | 3.7 |
| Ti pin | 14 weeks | 12.2 | 145.2 | 99.0 | 9.6 | 3.6 |
| Mg—Zn pin | 14 weeks | 11.3 | 146.8 | 100.6 | 9.4 | 3.3 |
| Ti cuff | 14 weeks | 11.6 | 147.6 | 99.6 | 9.2 | 3.3 |
| Mg—Zn cuff | 14 weeks | 12.2 | 148.0 | 99.8 | 8.7 | 3.5 |

ICP Analysis on Liver and Kidney

ICP analysis of the liver or kidney was performed to examine any form of Mg accumulation in the organs after implantation of the Mg—Zn alloy pins and cuffs in comparison to the Ti control. Mg concentration determined in the kidney harvested from the experimental groups containing Mg—Zn implants exhibited no accumulation of Mg when compared to the concentration of kidney from the non-operated groups. Mg concentration observed in the liver tissue from the non-operated controls was in the range of 521 µg of Mg per gram of dried tissue. Regardless of implantation time, Mg—Zn alloy groups implanted with pin did not show any significant difference with the control level in Mg concentration of liver samples. The observation was consistent with blood test results indicating that implantation of the Mg—Zn alloy pins and cuffs in the rat femoral model exhibited no systemic toxicity.

H&E Staining of Liver and Kidney

Figure 11:
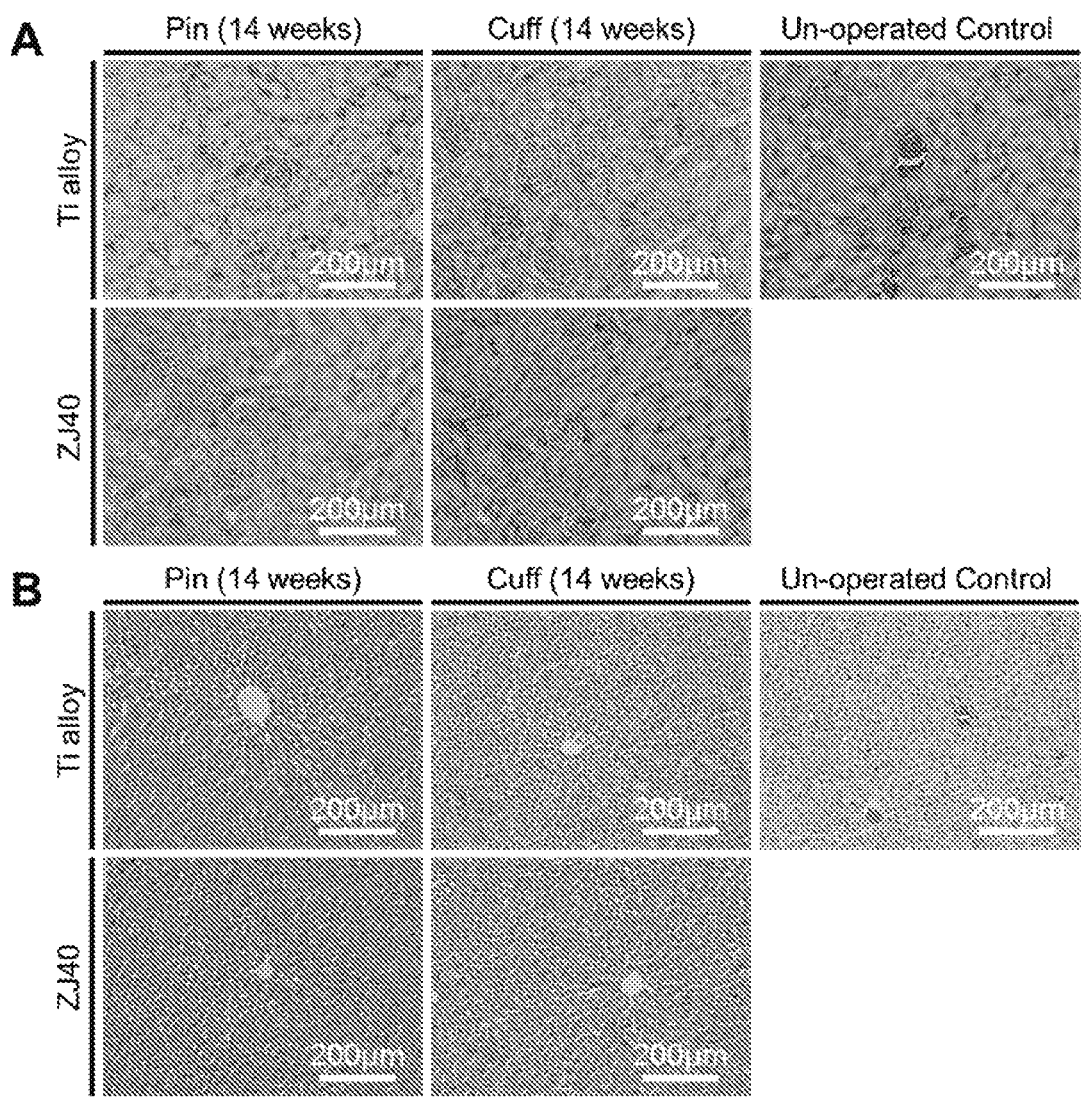
FIG. 11 is a plurality of hematoxylin and eosin staining of harvested (a) liver and (b) kidney, in accordance with certain embodiments of the invention.

Hematoxylin and eosin staining of liver and kidney tissue sections were performed to visualize any histological differences in tissue morphology due to Ti and Mg—Zn pin implantation. Liver sections of both Ti and Mg—Zn groups after 2 and 14 weeks of implantation, as shown in FIG. 11, exhibited a normal distribution of hepatocytes with clearly visible nuclei and central vein. In the kidney histology, no visible difference in glomeruli morphology, Bowman's space, capillaries, and convoluted tubules was observed between Ti control and Mg—Zn groups following 14 weeks of implantation. Histological morphology of liver and kidney tissues of all experimental groups displayed similar morphology as the non-operated control, and no difference was observed in between the groups or at different time points although data is not shown. In addition to ICP and blood test results, the H&E staining confirmed no damage to vital kidney and liver organs due to degradation following implantation of the biodegradable Mg—Zn pins. Although the H&E staining cannot be used to determine any accumulation of Mg, the fact that the histology showed normal and functional tissue was likely indicative of no accumulation related damage of the kidney and liver tissue, and potentially with time, there will be removal of Mg following the normal excretory process prevalent in the body.

Bone Tissue Histology

Figure 12:
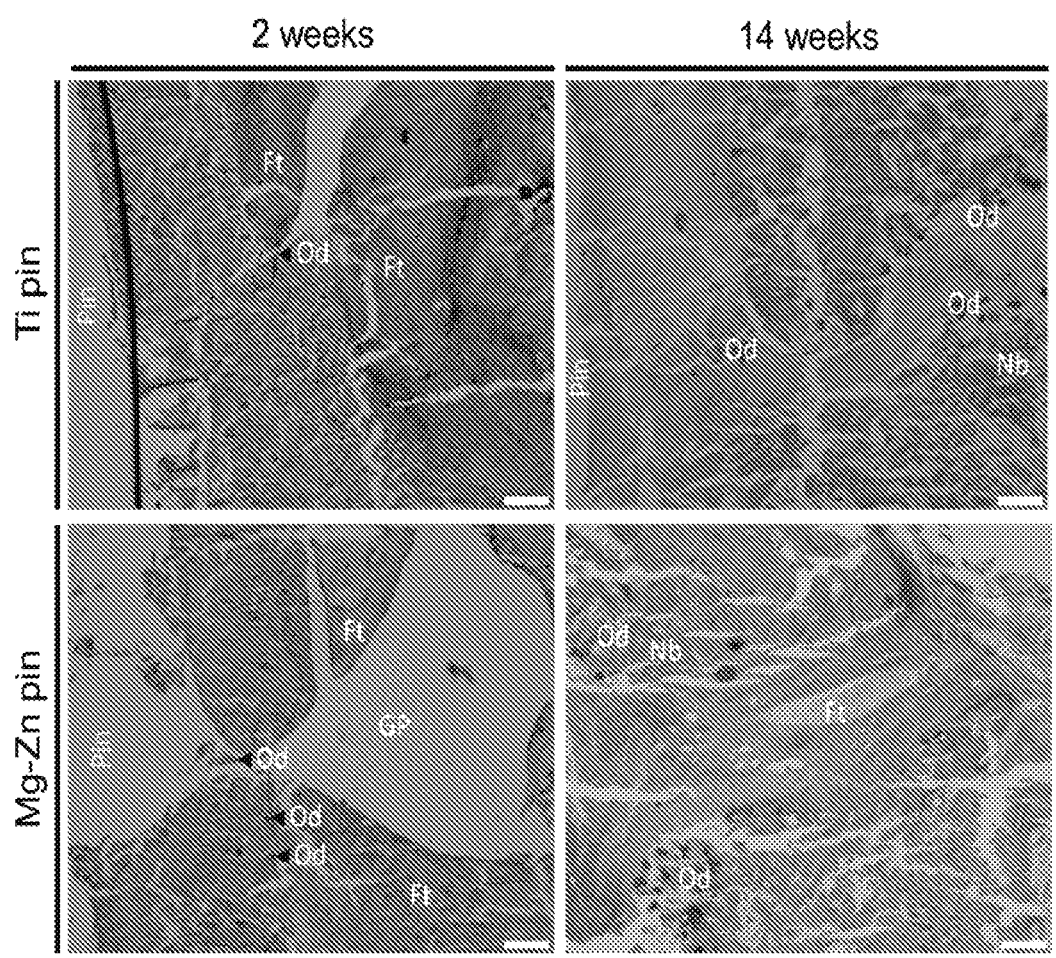
FIG. 12 is a plurality of images of Goldner's Masson Trichrome staining of rat femurs after implantation of Ti and mg-Zn pins for 2 and 14 weeks, in accordance with certain embodiments of the invention.
Figure 13:
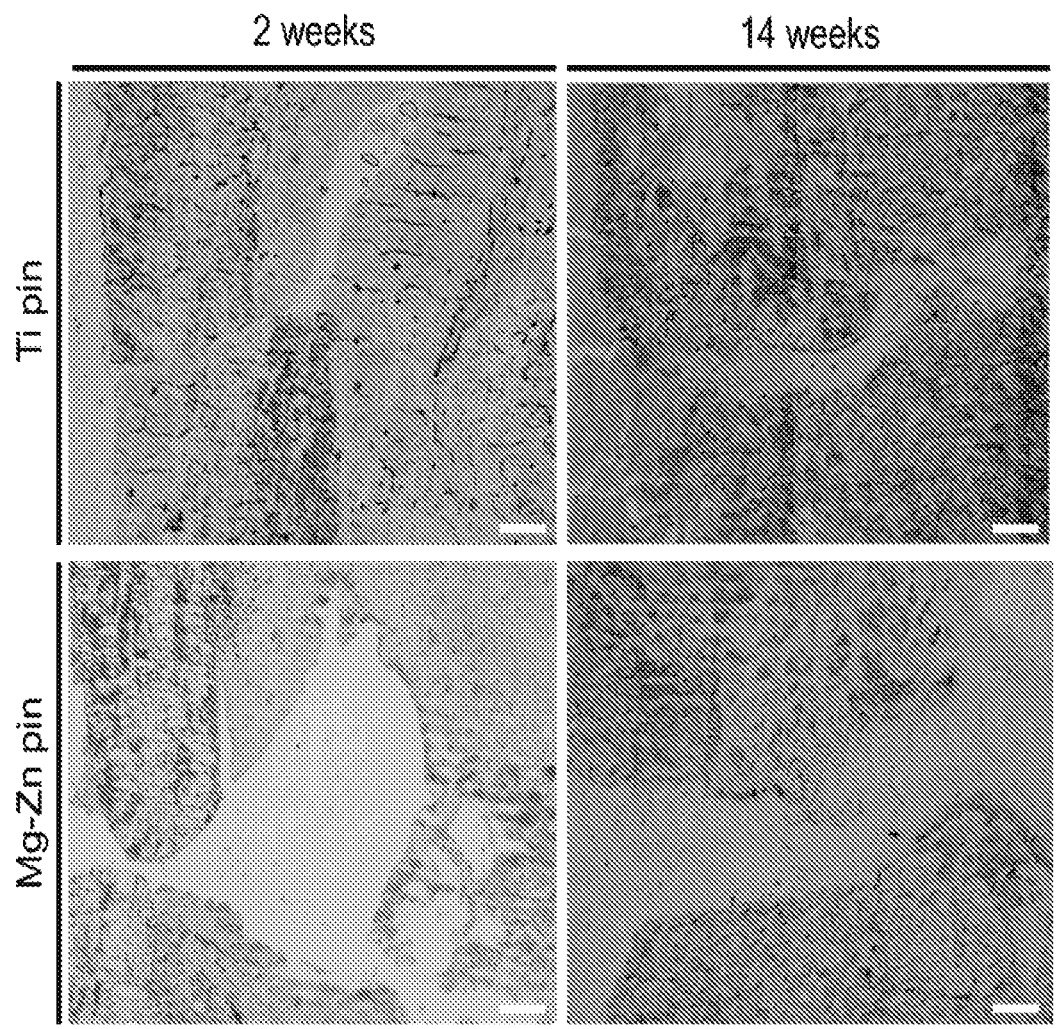
FIG. 13 is a plurality of images of alkaline phosphatase staining of rat femurs after implantation of Ti and Mg—Zn pins for 2 and 14 weeks, in accordance with certain embodiments of the invention.

Goldner's Masson Trichrome and alkaline phosphatase staining of rat femoral sections after plastic embedding revealed a typical fracture healing response as shown in FIGS. 12 and 13. After 2 weeks of implantation, the femurs with Ti and Mg—Zn alloy pins exhibited endochondral bone development and fibrous tissue formation around the fracture. Bone tissue section of the femur with Mg—Zn alloy pins after 2 weeks of implantation exhibited a gas pocket due to the degradation of Mg—Zn pins. After 14 weeks of implantation however, femurs with both Ti and Mg—Zn alloy pins exhibited bone remodeling and intramembraneous bone formation. In addition, the gas pocket of femurs with Mg—Zn pins was filled with fibrous tissues. Alkaline phosphatase activity (ALP) was observed around the fractured bones after 2 and 14 weeks of implantation. ALP was more present in the intramedullary region after 2 weeks. However, after 14 weeks, stained ALP signal was present along the fractured surface of the femurs, and stronger ALP activity was shown in the image of ALP staining of femoral tissue with Mg—Zn alloy. Fracture repair of either Ti or Mg—Zn groups was not completed after 14 weeks of implantation.

Discussion

Biodegradable Mg alloys have gained considerable attention as discussed earlier for their potential to provide comparable or even improved benefits in fracture repair, and for bone fixation compared to biodegradable polymer and permanent bioinert metallic devices. Mg is characterized by mechanical properties being matched to natural human bone. Alloys are designed to exhibit mechanical properties with better match to natural bone while exhibiting the desired timely corrosion rates with more biocompatible degradation products, as compared to biodegradable polymers that tend to provide acidic by-products while also lacking the desired osteogenic potential to function as an acceptable bone scaffold system. The rapid corrosion of biodegradable Mg alloys can cause hydrogen gas evolution and immature mechanical failure, warranting the need for improved alloy design and other surface engineered strategies to control the corrosion rates while preserving the mechanical strengths. Hence, in vivo degradation and toxicity of Mg alloys have been widely studied to demonstrate the much desired biosafety and efficacy as candidate biomaterials for implantable devices. Orthopedic devices are often used in load-bearing conditions and metals often tend to corrode more rapidly when stress is applied via the well-known stress corrosion mechanisms. This is a common fixture and often the mode of much observed problems to date in permanent metal devices which also reveal stress induced corrosion, wear, and debris formation.

The examples tested degradation properties and biocompatibility of Mg—Zn—Sr—Zr alloys under load-bearing condition. Mg alloys are not intended for use as a femoral rod since they are known to degrade in the body. However, a femoral fracture model using intramedullary pins can exert a significant load on the implant material to cause a stress-induced corrosion for examining relevant physiological response, such as bone healing, inflammatory response, and systemic toxicity. Thus, serving as an ideal model system to study the initial fracture healing response under the presence of stress. In addition to the fracture model, a group of rats were implanted with femoral cuffs for 14 weeks to compare any difference in systemic toxicity due to implantation site.

In vivo degradation of Mg—Zn pins and cuffs was assessed using x-ray radiographs after 1 week of surgery. It is widely accepted that hydrogen gas bubble evolves in the earlier time points and tend to kinetically slowdown in 2~3 weeks. Mg alloys implanted in bone without a significant load also are reported to show slow degradation exhibiting no gas bubbles, while Mg alloys in subcutaneous region exhibit significant gas bubbles due to the surrounding vascularization and presence of blood flow. Both Mg—Zn alloy pins and cuffs were observed to be surrounded with hydrogen gas in the surrounding tissue. Bone histology results were also consistent with the x-ray images showing gas pockets near the fracture site in the image following 2 weeks of Mg—Zn pin implantation (see FIG. 9). Both x-ray radiograph and bone histology results indicated that the corrosion of Mg—Zn alloy implants in rat femurs were rapid enough to create gas bubbles. However, the gas bubbles appeared to be eliminated after 14 weeks of implantation as shown in bone tissue histology images.

Computed tomography was used to perform fracture healing and determine quantitatively the degradation rate. Failure of the Mg—Zn alloy pins was observed in fractured femurs after 2 weeks of implantation. After 14 weeks, however, callus formation and bone remodeling around the fracture site were exhibited. Femurs with both Ti and Mg—Zn alloy pins revealed similar bone repair response. Rat femoral fracture models typically require up to 5 months to complete the fracture healing process. Three out of five rat femurs with implantation of Mg—Zn pins for 14 weeks were observed with a mal-union that might have resulted from the breakage of the pins due to the excessive stress experienced by the animals following immediate surgery, and allowing the rats to ambulate subjecting the area to significant load serving as a classic stress corrosion fracture model. The bone histology and CT results showed acceptable and favorable bone healing responses, as indicated by the other femurs in union exhibiting better bone healing with more bone remodeling and united callus formation over the cortical bones (See FIGS. 10, 12, and 13). These results demonstrate the potential safety and efficacy of the Mg—Zn alloy system for orthopedic applications.

Mg—Zn alloys are known to degrade with higher corrosion rates compared to Mg alloys under non-load bearing condition. Based on these results, rapid corrosion of Mg—Zn alloy pins under load-bearing conditions did not significantly affect the fracture repair in terms of adverse local tissue response. However, mechanical strength of Mg alloys decreases with corrosion and therefore, the Mg—Zn alloy pins underwent failure which could have affected the fracture healing outcome negatively. Although, not negating the potential applicability of the system for orthopedic applications.

Systemic toxicity of rats with Mg—Zn alloy pins was assessed after 2 and 14 weeks of implantation, when 15% and 55% of total volume of the implants were resorbed. In addition, a group of the Mg—Zn alloy cuffs was assessed to evaluate the toxicity of Mg—Zn alloy in contact with both bone and muscle. After 14 weeks, the cuffs were fully resorbed. Blood and serum examination was focused on hematologic and biochemical analysis to detect any disruption in blood, liver and kidney tissue state. Blood cell count and biochemical parameters were maintained within the reference ranges, and there were no significant difference among Ti, Mg—Zn, and control groups. Recent publications also reported no significant abnormality in blood test results following in vivo degradation of Mg alloys. BUN, CR, and UA from serum analysis also indicates no significant changes in the renal function. No accumulation of Mg in liver and kidney was also found following inductively couple plasma analysis conducted on the digested tissues. Histology of liver and kidney also displayed histomorphology pattern, mirroring healthy tissue. Excess Mg in body is known to excrete in urine after renal filtration. Bodily Mg concentration beyond the tolerance limit can, however, cause renal failure. Based on the published literature, the toxicity test methods described herein are effective because high Mg dose in body does not cause local accumulation in a specific organ other than liver or kidney. Overall, the observations from blood test, Mg concentration, and histology results consistently indicated that the Mg—Zn alloy implants and their degradation products are biocompatible for use as orthopedic implants under load-bearing conditions.

Conclusions

Mg—Zn alloy, in comparison to Ti alloy as a control, was examined as femoral pins under load-bearing conditions using a rat femoral fracture model. Localized stress on the Mg—Zn alloy pins caused stress corrosion. Hence, hydrogen gas pockets were observed around the fracture site initially, and some pins tended to lose their mechanical stability after the implantation for 2 weeks. However, normal bone healing was displayed following bone histological analysis. No fibrous capsule formation or adverse immune response was observed in local tissues around the Mg—Zn alloy implant devices as well. Furthermore, degradation of Mg—Zn implants caused no significant changes in hematologic or biochemical markers, assessed using blood panel tests. Magnesium concentration of liver and kidney demonstrated no accumulation of Mg in these organs, as well following elemental analysis of the tissue for the specific alloying elements. Histology of liver and kidney also displayed no organ damages due to the Mg—Zn alloy implants. Overall, the results suggest that Mg—Zn alloy demonstrates favorable biocompatibility under load-bearing conditions.

Example 3

An alloy labeled as WJ41 having the following composition: 4% Y, 0.6% Sr, 0.4% Zr and a remainder of Mg, was melted and cast using the method described below.

Ingots of elemental magnesium (99.97% pure from U.S. Magnesium, Inc.), and magnesium-yttrium master alloy (30 wt. % yttrium) were weighed according to the nominal composition. The ingots were melted together in a graphite crucible (200 g batch) inside a quartz tube of a vacuum induction furnace to preclude oxidation of the pure elements. The graphite crucible preloaded with batch and the quartz tube assembly were purged with UHP argon several times and vacuumed subsequently to achieve a moisture-free environment prior to induction melting. The induction melting then was conducted and repeated several times in order to achieve compositional homogeneity. The initial alloy produced by the induction melting was cleaned thoroughly from any residue or oxide scale and re-melted subsequently in a mild steel crucible using an electrical resistance furnace (from Wenesco, Inc.). The melting and pouring temperature was about 700° C., and once the temperature was reached, zirconium was added using Zirmax® (Mg-33.3% Zr) master alloy (from Magnesium Elektron, LTD.). The liquid melt was stirred for about 10 seconds after 1-minute and 5-minute intervals to dissolve and disperse the zirconium particles uniformly into the melt. Strontium was also added and melted. The melt was held for about 30 minutes at 700° C. and then poured onto a copper mold (1.5"×0.5") and a steel mold (2.0"×1.5") at room temperature. The as-cast samples were solution treated ("T4") at 525° C. for about 2 hours inside a tubular furnace covered with magnesium gettered powder under a protective atmosphere of argon and sulfur hexafluoride, and then quenched into water. Thin square plates (10×10×1 mm$^3$) of samples were sectioned (using a Buehler Precision Saw Simplimet 1000) from the as-cast and the T4 samples, and were characterized by X-ray diffraction (XRD) using Philips XPERT PRO system employing the CuKα (λ=1.54056 Å) radiation operated at 45 kV and 40 mA to determine the phase evolution and formation. The thin plate samples from the as-cast and T4 conditions were also used for electrochemical corrosion tests. Each square plate sample was mechanically grinded and polished to 2000 grit; ultrasonically cleaned in acetone, absolute ethanol and distilled water; and then dried in a vacuum oven at a temperature of 50° C.

The cast material demonstrated single phase Mg according to the X-ray diffraction pattern, without indication of the presence of secondary phases, which clearly confirmed the formation of single phase solid solution.

However, microstructure analysis using optical microscopy and scanning electron microscopy (SEM) with energy dispersive spectroscopy (EDS) revealed the presence of secondary phases containing Mg, Y, Zr and Mg, Al (an impurity), Sr, and Y.

Potentiodynamic corrosion tests were carried out using a scanning rate of 1 mV/s. A three-electrode cell was employed with platinum as the counter electrode, Ag/AgCl as the reference electrode, and the sample mounted in epoxy resin as the working electrode. The test was performed in Hank's Balanced Salt Solution (HBSS) and held at 37.4° C. Before each measurement, the sample was immersed in the corrosion media to provide stability. The cathodic and anodic portions of the generated Tafel plots were fit linearly to allow the calculation of corrosion potential, $E_{corr}$, and the corrosion current density, $i_{corr}$, which was used to calculate corrosion rate according to ASTM G102-89, with the results as reported in Table 1C. The corrosion rate for the WJ41 cast alloy was slightly higher than the commercially obtained as-drawn pure Mg.

TABLE 1C

Electrochemical corrosion results of WJ41 alloy compared to pure Mg.

| | Corrosion potential (V) | Corrosion current density (μA/cm$^2$) | Corrosion rate (mm/yr) |
| --- | --- | --- | --- |
| WJ41 as-cast | −1.51 ± 0.02 | 6.60 ± 0.82 | 0.15 ± 0.02 |
| Pure Mg as-drawn | −1.49 ± 0.01 | 4.38 ± 0.26 | 0.10 ± 0.01 |

The Mg—Y—Sr—Zr alloy (WJ41) after casting exhibited secondary phases containing Mg, Y, Zr and Mg, Al, Sr, and Y. The presence of these secondary phases may have resulted in the slightly increased corrosion rate compared to pure Mg. It is expected that extrusion would improve the corrosion rate of WJ41.

Example 4

The effect of adding Sr to Mg—Zn—Zr (designated as ZK40) was further demonstrated using the following results of Mg—Zn—Zr—Sr (designated as ZJK40 and ZJK41). A comparison of the mechanical, corrosion, and cytocompatibility properties were studied for Mg—Zn—Zr (ZK40) and Mg—Zn—Zr—Sr (ZJK40 and ZJK41), which were processed using the same conditions as described in Example 3. An alloy with the addition of Zn to the Mg—Y—Zr—Ca system (WZKX42 alloy) was also compared to the other alloy systems. For cytotoxicity tests, samples were sterilized by ultraviolet radiation for about 1 hour. The below results show that the addition of Sr resulted in a significant improvement in corrosion resistance as demonstrated by immersion corrosion data while there was no deterioration in the mechanical properties or cytocompatibility.

TABLE 2C

Mechanical Properties of the new alloys containing Sr (ZJK), Zn (ZK), and Y—Zn—Ca—Zr (WZKX42) following improved processing.

| Alloy | Young's Modulus (GPa) | Yield Strength (MPa) | Ultimate Tensile Strength (MPa) | Percent Elongation (%) |
|---|---|---|---|---|
| Commercial AZ31 | 55 | 202 | 268 | 12 |
| Pure Mg | 5 | 19 | 66 | 7 |
| ZK40 as-cast | 64 | 96 | 176 | 4 |
| ZK40 T4 | 68 | 92 | 83 | 2 |
| ZK40 as-extruded (Mg—Zn—Zr) | 45 | 287 | 327 | 9 |
| ZJK with 0.1% Sr (Mg—Zn—Zr—Sr) ZJK40 | 42 | 293 | 317 | 13 |
| ZJK with 1% Sr (Mg—Zn—Zr—Sr) ZJK41 | 41 | 293 | 321 | 10 |
| WZKX42 (Mg—Y—Zn—Zr—Ca) | 52 | 334 | 412 | 14 |

Mechanical properties of the magnesium alloys used for K-wires were determined using tensile testing. High strength materials of titanium and stainless steels are currently used in K-wires to sustain loads placed on the device to maintain fracture union. Thus, magnesium alloys used to replace these inert metals should also have high strength. Table 2C shows the Young's modulus, tensile strength, and elongation of the strontium-containing magnesium alloys compared to commercially available pure Mg and Mg—Al—Zn (designated AZ31B) magnesium alloy (Goodfellow Corporation, USA), as well as the alloys ZK40 and Mg—Y—Zn—Zr—Ca (designated WZKX42), which have an absence of strontium. The inventive alloys belonging to the ZJK series exhibited significantly higher yield and ultimate tensile strength compared to pure Mg and AZ31. It is important to note that earlier alloys were not extruded while the new alloys have been, which partially contributed to the increase in strength, along with the selection of alloying elements, e.g., the presence of strontium. The high strength of WZKX42 was attributed to the addition of Zn which facilitates the formation of precipitates arranged in a long period stacking order (LPSO), an important factor contributing to impeding the movement of dislocations and enhancing the mechanical strength. The increase of strength of the new alloys is significant to support the favorable use of these alloys in claims of applications in various medical devices which particularly require high strength.

Vickers microhardness was measured by applying a load of 100 g for 10 s to polished Mg samples and measuring the indentation using optical microscopy. Microhardness of the strontium-containing and WZKX42 alloys were higher than both commercially available Mg and AZ31B alloy.

Cell viability of MC3T3-E1 pre-osteoblast cells cultured in media containing degradation products from 3 days of alloy immersion was determined using the MTT assay. Extract media from alloys was prepared in accordance with ISO Standard 10993:12. High cell viability was observed, with at least 75% cell viability observed for all alloys at 10% and 25% dilution of extract after culturing cells with the extract for 1 day and 3 days.

In vitro immersion corrosion measurements were performed in Hanks' Balanced Salt Solution (HBSS) to assess the corrosion rates of strontium-containing biodegradable magnesium alloys. Commercially available AZ31B and pure Mg were used as control groups in this study. Commercial extruded AZ31B exhibited the lowest corrosion rate (~0.05 mmpy) and the magnesium alloys exhibited comparable corrosion resistance.

Example 5

Pure Mg, Al, Zn, Ca and Mn were melted at 720° C. under a protective environment of Ar+0.1% $SF_6$ and poured into steel molds preheated at 500° C. The compositions were measured using inductively coupled plasma-optical emission spectroscopy (ICP-OES) and reported in Table 3. The as-cast ingots (AZXM-AC) were then T4 heat treated (AZXM-T4) at 385° C. in Ar atmosphere for 10 h to solubilize any intermetallics and alloying elements in the alloy matrix. The T4 heated ingots were extruded (AZXM-EX) at 300° C. with an extrusion speed of 1 mm/s followed by quenching in water. To study the in vitro degradation behavior of AZXM alloy, round shape plates with a diameter of 10 mm and thickness of 2 mm were immersed in Hanks' solution for 1, 2 and 3 weeks according to the ASTM G31 standard. Corrosion rate was calculated based on weight loss and the corrosion layer was studied under SEM/EDX. Dog-bone shaped samples were machined for tensile testing. Mechanical properties were measured using the Instron 5900 testing system equipped with an extensometer measuring the elongation. For primary cytotoxicity evaluation, MTT test was conducted on BEAS-2B cell line (human bronchial epithelial cells).

TABLE 3C

Chemical composition of AZXM alloy.

|  | Al | Zn | Ca | Mn | Mg |
|---|---|---|---|---|---|
| Nominal Composition (wt. %) | 2% | 1% | 0.6% | 0.2% | Bal. |
| Chemical Composition (wt. %) | 1.92% | 1.05% | 0.56% | 0.02% | Bal. |

The grain size of as cast AZXM alloy was about 300 μm and did not significantly change after T4 treatment. However, the grains were greatly refined after conducting hot extrusion. In the transverse direction, typical undefined grains characteristic of extrusion are visible due to severe plastic deformation. The grains were elongated along the extrusion direction.

AZXM as cast exhibited poor corrosion resistance and exhibited the highest corrosion among all of the test groups. T4 treatment however improved the corrosion resistance.

The corrosion resistance of AZXM alloys was also significantly improved after extrusion and is also not significantly different from the corrosion rate of AZ31 alloy. ICP data of $Mg^{2+}$ show concentration profiles similar to the corrosion rates from different test groups. However, in some groups, the accumulation of $Mg^{2+}$ was reversed after 2 weeks of immersion because of the deposition of the degradation product. Compared to AZ31, even though the corrosion rate of extruded AZXM was slightly higher, the overall corrosion appeared to be more uniform with the formation of $Mg(OH)_2$ based on an EDAX analysis. Pitting is the primary corrosion mode exhibited on the AZ31 surface due to the microstructure generated by the extrusion process.

Mechanical properties (Table 4C) were also significantly improved after extrusion due to the grain refinement following extrusion. The increase in Young's modulus and strength will be useful in providing enable better mechanical support for the fabricated stents, and the improved ductility would certainly help in preventing fracture as a result of the expansion of the stent.

TABLE 4C

Mechanical properties of AZXM alloy.

| | Young's Modulus (GPa) | Yield Strength (MPa) | Ultimate Strength (MPa) | Elongation at Fracture (%) |
|---|---|---|---|---|
| AZXM-AC | 23.80 ± 5.20 | 90.75 ± 7.39 | 129.00 ± 12.68 | 3.63 ± 0.37 |
| AZXM-T4 | 31.09 ± 0.19 | 84.20 ± 9.28 | 133.83 ± 9.75 | 3.53 ± 1.03 |
| AZXM-EX | 38.19 ± 4.26 | 233.53 ± 4.15 | 283.08 ± 1.72 | 8.56 ± 2.05 |

Viability of BEAS-2B cells was extremely low when cultured in 100% extract both on day 1 and day 3. However, the cell viability significantly increased when the extract was diluted. The dilution ratio and culture time did not significantly affect the cell viability. This result implies that the impact of AZXM stent on tracheal tissue may be limited, since the degradation product will be diluted by the mucus that continuously flows through the airway.

AZXM alloy exhibits potential for use as degradable intra-luminal stents for tracheal obstructions. Extruded AZXM alloy shows less pitting, higher corrosion resistance and optimized mechanical properties. Future plans for clinical translation would include intra-luminal tracheal stent design and manufacture, as well as in vivo evaluation in rabbit tracheal stenosis model.

Example 6

A rat femoral fracture model was used to assess the performance and toxicity of modified-ZK40 (M-ZK40) and Mg—Y—Zn based alloys.

M-ZK40 and Mg—Y—Zn based alloy rods were inserted into the intramedullary cavity to repair a full osteotomy in the midsection of rat femurs. Ti-6Al-4V rods were used as the negative control. After 7 days, X-ray imaging was performed to confirm the location of the rods. Blood was drawn to perform blood cell counts and serum biochemical test prior to implantation and after sacrifice at 14, 56 and 84 days. After sacrifice, femurs were explanted and μCT was used to observe the surrounding bone and measure the degradation rates of the Mg alloy rods. Local tissue response and bone healing was assessed by histology with Goldner's Trichrome staining. Potential systemic toxicity in the liver and kidney was evaluated by H&E staining and measurement of alloying elements by ICP-OES.

X-ray images of the metallic rods used to fix the full osteotomy demonstrated the placement of the rods in the middle of the femoral intramedullary cavity to align the bone fragments and fix the defect. Blood test results exhibited no significant difference between groups or time points. Blood cell counts, liver and kidney functional parameters, phosphorous, chloride, magnesium, and potassium levels at 0, 14, 56 and 84 days were within the normal range. No sign of accumulation of degradation products or toxicity were observed in liver and kidney histology and elemental analysis. Indications of corrosion were observed at high stress regions near the fracture site, suggesting the onset of stress corrosion cracking. μCT images after 2 weeks exhibited some breakage of rods in both M-ZK40 and Mg—Y—Zn groups. Despite the fragmentation of the mg alloy rods, new bone formation was observed between the ends of the fragmented femurs.

In order to demonstrate the degradation of m-ZK40 and Mg—Y—Zn rods under load-bearing conditions, a rat femoral fracture model was employed. Breakage of rods and indications of corrosion were observed. However, the Mg alloy rods did not appear to cause significant toxicity, with no significant difference between groups and time points shown in blood, liver, and kidney analyses.

The invention claimed is:

1. An orthopedic or craniofacial bone fixation component composed of an extruded biodegradable, magnesium alloy, consisting of:
   from 0.5 weight percent to 4.0 weight percent of yttrium;
   from greater than zero to 1.0 weight percent of calcium;
   from 1.0 weight percent to 6.0 weight percent of zinc;
   from greater than zero to 1.0 weight percent of zirconium;
   from 0.10 weight percent to 6.0 weight percent of strontium;
   and
   a balance of magnesium and impurities due to production, based on total weight of the alloy,
   wherein the orthopedic or craniofacial bone fixation component is selected from the group consisting of Kirschner wire, cerclage wire, intramedullary rod, and intramedullary pin, and
   wherein the extruded biodegradable, magnesium alloy has formed precipitates arranged in a long period stacking order.

2. An orthopedic or craniofacial bone fixation component composed of an extruded biodegradable, magnesium alloy, consisting of:
   from 1.0 weight percent to 6.0 weight percent of zinc;
   from greater than zero to 1.0 weight percent of zirconium;
   optionally from greater than zero to 6.0 weight percent of strontium;
   optionally from 1.0 weight percent to 9.0 weight percent aluminum;
   optionally from 0.1 weight percent to 1.0 weight percent of manganese;
   optionally from 0.25 weight percent to 1.0 weight percent of silver;
   optionally from 0.1 weight percent to 1.0 weight percent of cerium; and
   a balance of magnesium and impurities due to production, based on total weight of the alloy,
   wherein the orthopedic or craniofacial bone fixation component is selected from the group consisting of Kirschner wire, cerclage wire, intramedullary rod and intramedullary pin, and
   wherein the extruded biodegradable, magnesium alloy has formed precipitates arranged in a long period stacking order.

* * * * *